US00RE50096E

(19) United States
(12) Reissued Patent
Egan et al.

(10) Patent Number: US RE50,096 E
(45) Date of Reissued Patent: *Aug. 27, 2024

(54) NANOEMULSION COMPOSITIONS OF TAXOID DRUGS, AND METHODS FOR THE USE THEREOF TO TARGET CANCER CELLS AND CANCER STEM CELLS

(71) Applicants: TargaGenix, Inc., Stony Brook, NY (US); The Research Foundation for the State University New York, Albany, NY (US); Northeastern University, Boston, MA (US)

(72) Inventors: James E. Egan, Stony Brook, NY (US); Iwao Ojima, Port Jefferson, NY (US); Mansoor M. Amiji, Attleboro, MA (US); Galina Ivanovna Botchkina, Stony Brook, NY (US)

(73) Assignees: The Research Foundation for the State University New York; Targagenix, Inc., Stony Brook, NY (US); Northeastern University, Boston, MA (US)

( * ) Notice: This patent is subject to a terminal disclaimer.

(21) Appl. No.: 17/179,720

(22) Filed: Feb. 19, 2021

Related U.S. Patent Documents

Reissue of:
(64) Patent No.: 10,206,875
Issued: Feb. 19, 2019
Appl. No.: 15/616,103
Filed: Jun. 7, 2017

U.S. Applications:
(60) Provisional application No. 62/346,755, filed on Jun. 7, 2016.

(51) Int. Cl.

| | |
|---|---|
| ***A61K 9/107*** | (2006.01) |
| ***A61K 9/51*** | (2006.01) |
| ***A61K 31/337*** | (2006.01) |
| ***A61K 47/12*** | (2006.01) |
| ***A61K 47/44*** | (2017.01) |
| ***A61K 47/54*** | (2017.01) |
| ***A61K 47/69*** | (2017.01) |

(52) U.S. Cl.
CPC ..... *A61K 9/1075* (2013.01); *A61K 9/51* (2013.01); *A61K 31/337* (2013.01); *A61K 47/12* (2013.01); *A61K 47/44* (2013.01); *A61K 47/542* (2017.08); *A61K 47/6907* (2017.08)

(58) Field of Classification Search
CPC ..... A61P 35/00; A61P 43/00; A61K 47/6907; A61K 9/1075; A61K 9/0019; A61K 47/12; A61K 35/02
See application file for complete search history.

(56) References Cited

U.S. PATENT DOCUMENTS

| | | | | |
|---|---|---|---|---|
| 7,820,839 | B2 * | 10/2010 | Ojima | A61P 35/00 549/511 |
| 2006/0067952 | A1 * | 3/2006 | Chen | A61K 9/0019 424/400 |
| 2007/0088076 | A1 * | 4/2007 | Ojima | A61K 47/48038 514/449 |
| 2007/0148194 | A1 * | 6/2007 | Amiji | A61K 9/0095 424/400 |

OTHER PUBLICATIONS

Botchkina et al. Molecular Cancer 2010, 9:192: pp. 1-12 (Year: 2010).*
Botchkina et al. Plos One. Sep. 2012. vol. 8, Issue 9.pp. 1-16. (Year: 2013).*
Dragu et al (World Journal of Stem Cells, 2015, vol. 7, pp. 1185-1201).*
Han et al (Acta Pharmaceutica Sinica B, 2013, vol. 3, pp. 65-75).*
Seaworth et al (Microbiology Spectrum, 2017, Therapy of Multidrug-Resistant and Extensively Drug-Resistant Tuberculosis).*
Housman et al (Cancers(Basel), 2014, vol. 6, pp. 1769-1792).*
Botchkina et al (Plos One, 2013, vol. 8, pp. 1-16).*

* cited by examiner

*Primary Examiner* — Padmashri Ponnaluri
(74) *Attorney, Agent, or Firm* — Kohn & Associates PLLC; Kenneth I. Kohn; Laura S. Dellal

(57) ABSTRACT

A composition of an omega-3 polyunsaturated fatty acid (PUFA)-taxoid conjugate encapsulated in an oil-in-water nanoemulsion (NE) drug delivery system. A method of treating cancer by administering an effective amount of a pharmaceutical composition including a PUFA-taxoid conjugate encapsulated in an oil-in-water NE drug delivery system to a subject in need of treatment, and treating cancer. A method of overcoming multidrug resistance by exposing a multidrug resistant cell to an effective amount of a pharmaceutical composition including an omega-3 polyunsaturated fatty acid (PUFA)-taxoid conjugate encapsulated in an oil-in-water NE drug delivery system, and inducing the death of the multidrug resistant cell. A method of eliminating a cancer stem cell. Methods of reducing stemness of a cancer stem cell, retaining drug in the body, and providing a slower release profile.

76 Claims, 24 Drawing Sheets wherein $R^1$ is cyclopropyl, $R^2$ is 2-methyl-1-propenyl, and $R^3$ is H.

NE-Placebo

NE-DHA-ABT-1214

Abraxane

Size Distribution by Intensity

Zeta Potential Distribution

FIG. 9A
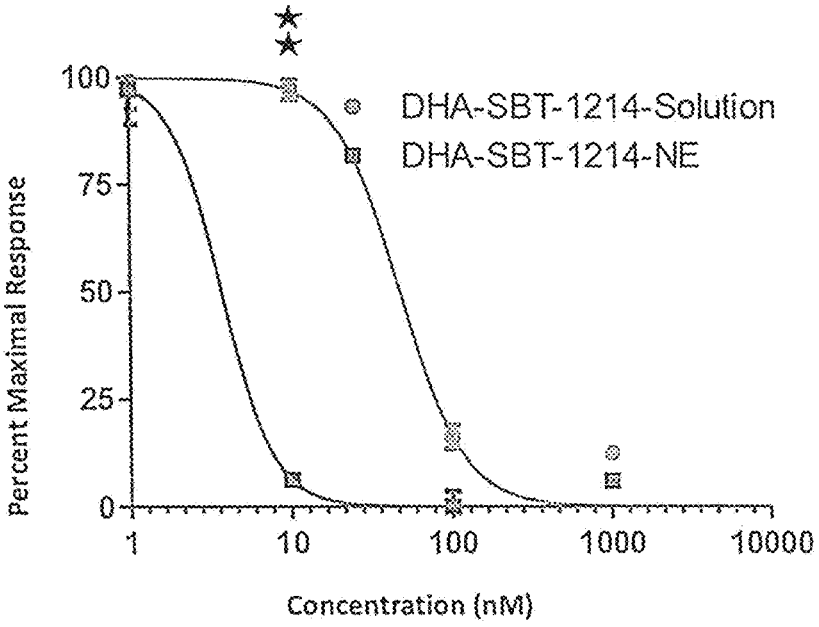
FIG. 9B
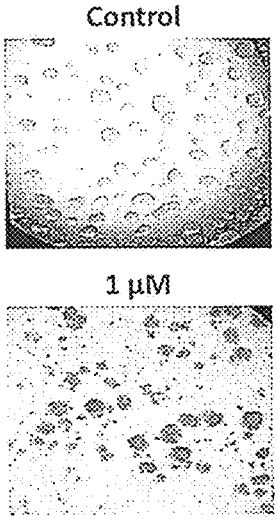
FIG. 9C
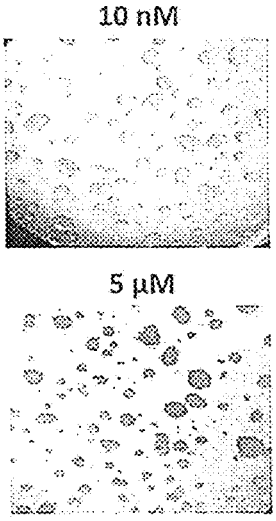
FIG. 9D
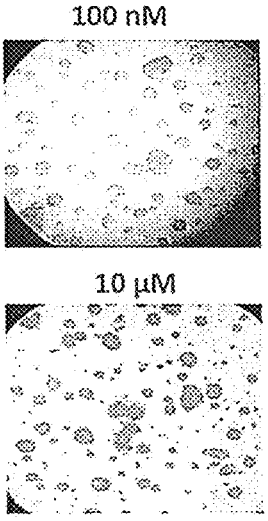
FIG. 9E
FIG. 9F
FIG. 9G FIG. 11A
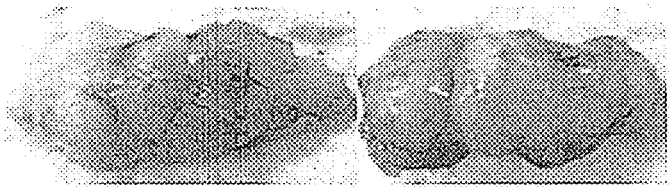
FIG. 11B
FIG. 11C
FIG. 11D
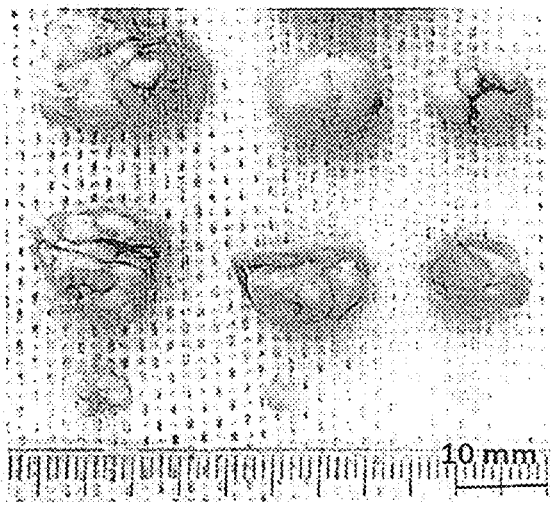
FIG. 11E
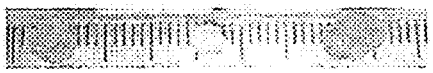
FIG. 11F
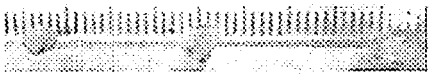
FIG. 11G
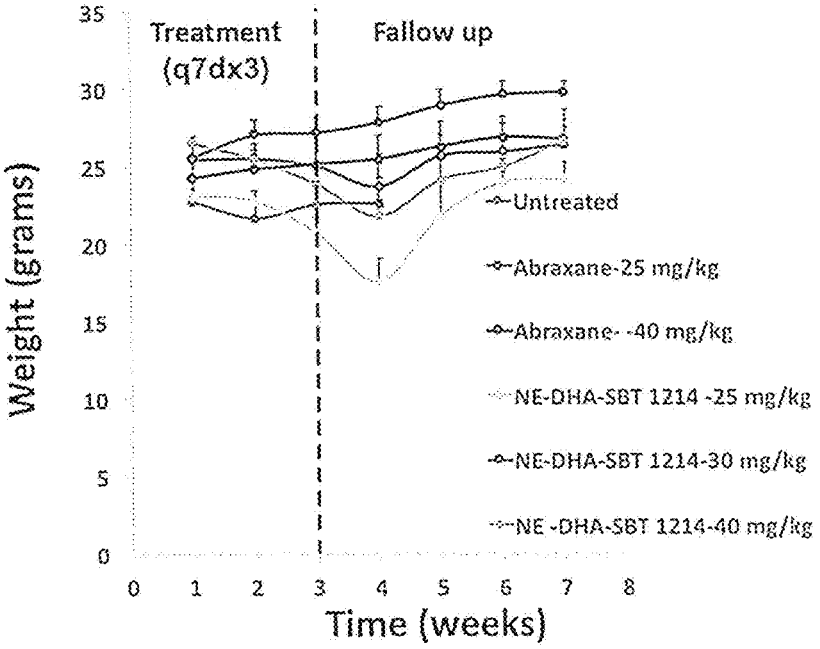

FIG. 14A
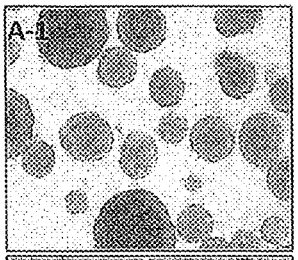
FIG. 14B
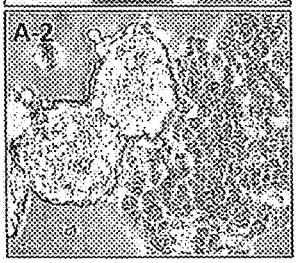
FIG. 15A
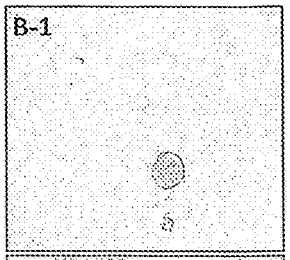
FIG. 15B
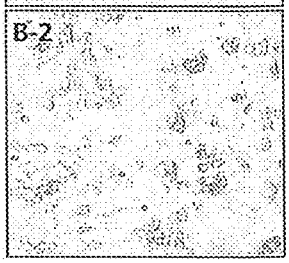
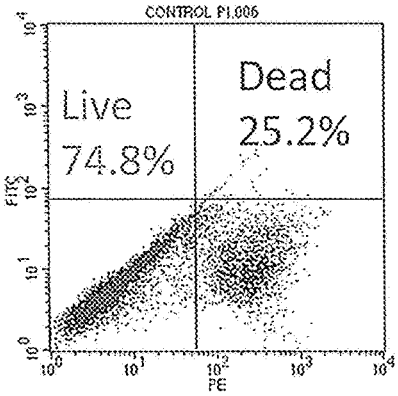
FIG. 16
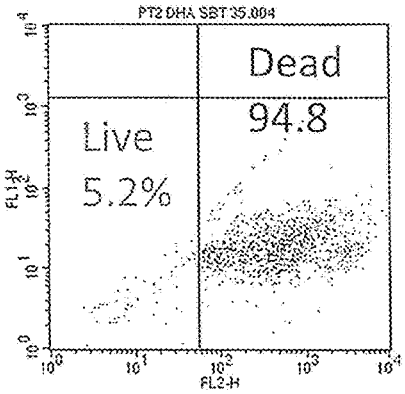
FIG. 17

Biodistribution of DHA-SBT-1214 solution or nanoemulsion
Brain
Pancreas
Kidney
Prostate
Solution
NE
DHA-SBT-1214 Concentration (µg/g)
Time (h)

Biodistribution of DHA-SBT-1214 solution or nanoemulsion
Colon
Solution
NE

Heart
Solution
NE

Lung
Solution
NE

Liver
Solution
NE

DHA-SBT-1214 Concentration (µg/g)
Time (hours)

Biodistribution of DHA-SBT-1214 solution or nanoemulsion

Tumor suppression with the NE-DHA-SBT-1214 after 4 weeks follow-up

Control Untreated 30 mg/kg x3 weekly 40 mg/kg x3

50 mg/kg x3

70 mg/kg x2

**Note: Control untreated tumors have reached >6300 $mm^3$ (average) by $6^{th}$ week.

NANOEMULSION COMPOSITIONS OF TAXOID DRUGS, AND METHODS FOR THE USE THEREOF TO TARGET CANCER CELLS AND CANCER STEM CELLS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This application is a reissue of U.S. application Ser. No. 15/616,103, filed Jun. 7, 2017, now U.S. Pat. No. 10,206,875, filed Feb. 19, 2019, which claims the benefit of U.S. Ser. No. 62/346,755, filed Jun. 7, 2016, the entire contents of which is herewith incorporated by reference in its entirety for all purposes.*

GRANT INFORMATION

This invention was made with government support under CA103314, CA132396 and HHSN261201500018C awarded by the National Institutes of Health. The government has certain rights in the invention.

TECHNICAL FIELD

The invention relates to therapeutic agents and methods for treating cancer, and especially for overcoming multidrug resistance, including multidrug resistance in cancer stem cells. In particular, the invention relates to nanoemulsion formulations and delivery systems for taxoid drugs, such as third-generations taxoids.

BACKGROUND OF THE INVENTION

Cancer is the second leading cause of death in the United States. In contrast to other human cancers, incidence and death rates of prostate cancer (PrC) have significantly increased in the current decade. More than 70% of PrC patients will face post-treatment recurrence and transition of the disease to an incurable state. It is largely accepted that human tumors are organized hierarchically, and that the top of this hierarchy is occupied by malignant stem cells, which possess unlimited self-renewal and tumor-initiating capacities. According to the most recent concept of carcinogenesis, only specific phenotypic subpopulation(s) of cancer stem cells (CSCs) are responsible for tumor development, and for the production of the entire spectrum of the differentiated progeny that compose a tumor mass, including metastatic and drug resistant cells. CSCs have been isolated from all major human cancer types, including colorectal, pancreatic and prostate cancers. Numerous studies on many cancer types have demonstrated that the tumorigenic cells expressing common CSC markers, in particular CD133 and CD44, are exceptionally resistant to conventional anti-cancer drugs (such as 5-FU, oxaliplatin, irinotecan, docetaxel and others).

Multidrug resistance (MDR) to conventional and novel chemotherapeutic agents represents a formidable challenge for clinical cancer therapy. While MDR is not exclusively a property of CSC, a great deal of evidence shows that MDR is intimately associated with the presence of CSC. CSCs are naturally resistant to chemotherapy due to multiple mechanisms, including their relative quiescence, their profound capacity for DNA repair, their activation of the ATP-binding cassette (ABC) transporters that efflux many standard anti-cancer agents, and their resistance to apoptosis. The quiescence of CSCs also promotes their resistance to chemotherapy and radiation therapy. Moreover, the majority of standard anti-cancer drugs actually stimulate quiescent CSCs to self-renew and repopulate the tumor with drug resistant cells. CSC also show a number of phenotypic properties that are critical for the tumor phenotype, such as unrestricted cell replication, self-sufficiency and long-term survival. These properties help to explain why many cancer therapies, while killing the bulk of mature tumor cells, often fail, because they do not eradicate CSCs. Current prostate cancer treatments primarily target the bulk neoplastic, fast-growing cancer cells but not the CSCs subpopulation, and this could provide the reason for the limited survival benefits seen with most prostate cancer therapies. A surviving fraction of CSCs makes tumor recurrence almost inevitable following an apparently successful de-bulking by surgical resection and/or radiation and chemotherapy.

The fact that most cancer drugs do not address the CSC subpopulation explains the fact that the anticancer drugs in development have the highest attrition rate as compared to other diseases: only 5% of agents that have anticancer activity in preclinical development make it through to regulatory approval and even then may only have a small benefit. In particular, current anti-cancer drugs in development for prostate cancer have a significantly lower success rate as compared to other cancers. On the other hand, preclinical evaluation of candidate anticancer agents is traditionally based on the use of unselected high-passage commercial cancer cell lines grown as a monolayer culture. However, long-term in vitro maintenance inevitably leads to the accumulation of additional genomic and epigenomic changes, as well as to the selection of dominant cell subpopulations. Indeed, it was recently demonstrated that the most commonly used established cancer cell lines have no or low correlation with the original clinical samples. This suggests that the use of established cell lines for the study of genomic alterations, discovery of clinically relevant molecular targets, and anticancer drug development is questionable, since the use of these cell lines does not account for the complexity and pathophysiology of in vivo tumors. All of the above considerations highlight the crucial role of CSCs in the discovery of clinically relevant molecular targets and creates an urgent need for CSC-targeted drug development, more physiologically and clinically relevant sources of cancer cells, as well as more relevant in vitro and in vivo models.

Recently, Applicants have established patient-derived ultra-low passage prostate cancer cell line with stable retaining of the features of immature, stem-like cells (PPT2 cell line). The previous studies have demonstrated that the $CD133^{hi}/CD44^{hi}$ phenotype of prostate cancer cells showed clear stem cell-related features, including high tumor- and spheroid-initiating capacities, plasticity (ability to produce multiple cell phenotypes), and high resistance to standard drugs. These cells express over-activated developmental pathways and express high levels of several key transcription factors determining embryonic stem cell pluripotency. In addition, the PPT2 cells express many genes related to anti-apoptotic signaling and drug resistance, which make them a good model for CSC-targeted drug development studies.

Recent studies by Weinberg, Lander, and other groups have shown the tremendous plasticity for cancer cells to interconvert between differentiated tumor and cancer stem cell (CSC) phenotypes. Clinical research efforts show that cells with phenotypic-CSC markers are more prevalent after treatment with traditional chemotherapeutic agents, and are more tumorigenic than their differentiated counterparts. CSCs exist in 'meta-states' with significant plasticity, so that these cells can differentiate into cells that are tumorgenic and are either chemosensitive or MDR resistant.

This information suggests a need for therapies that address a number of "meta-phenotypic" states, and are multimodal, in order to mitigate MDR-mechanisms arising from both differentiated tumor cell and CSC populations. First-generation taxoid drugs, such as paclitaxel (PX) and docetaxel, do not meet this need. Taxoid drugs stabilize microtubules and inhibit late G2 or M phases of cell cycle, thereby causing the cell death. Although very active clinically, PX and docetaxel have several clinical problems including poor drug solubility, serious dose-limiting toxicities such as myelosuppression, peripheral sensory neuropathy, allergic reactions, and eventual development of drug resistance. A number of these side effects have been associated with the solvents used for dilution of these antineoplastic agents: Cremophor EL for paclitaxel and polysorbate 80 for docetaxel. In addition, reports have linked these solvents to undesirable alterations in PX and docetaxel pharmacokinetic profiles. A major drawback of the first generation taxoids is there ineffectiveness against MDR cells. These drugs are substrates of P-glycoprotein (Pgp), an effective ATP-binding cassette (ABC) transporter, which actively pumps the drugs out of the cells and induces drug resistance. This helps to explain why PX and docetaxel are effective initially against breast, ovary, and lung cancers, but do not show efficacy against colon, pancreatic, melanoma, and renal cancers. For example, human colon carcinoma is inherently multidrug resistant due to the over expression of Pgp. Accordingly, PX does not show any appreciable efficacy against human colon cancer xenografts in mice.

Second-generation taxoids offer an improved solution to the problems of MDR and CSCs. In sharp contrast with PX, a number of second-generation taxoids, such as SBT-1214, show excellent activity (2-3 orders of magnitude more potent than PX) against drug resistant cancer cells, expressing MDR phenotypes. In several studies using colorectal and prostate cancer models, SBT-1214 was shown to effectively kill both CSCs in vitro and in xenograft models. SBT-1214 was also found to possess intrinsic Pgp modulating ability. SBT-1214, exhibited remarkable efficacy against highly several drug resistant (Pgp+) colon tumor xenografts in SCID mice, inducing complete regression in all surviving mice with tumor growth delay>187 days. The observed total suppression of tumor recurrence by SBT-1214 may indicate that this taxoid can kill or regulate CSCs. Thus, we examined the activity of SBT-1214 against colon CSCs from HCT116, HT-29 and DLD-1 cell lines using cancer spheroids in 3D cultures. Administration of 100 nM SBT-1214 to the HCT116, HT-29 and DLD-1 spheroids for 48 h resulted in marked suppression of the growth of the secondary spheroids in all cells. Most importantly, viable cells that survived this treatment regimen significantly lost the ability to form secondary spheroids, which indicates that colon CSC population was critically affected. Also, it was found that the treatment of HCT116, DLD-1 and HT-29 CSCs with SBT-1214 led to the down-regulation of a number of stem cell-related genes and significant inhibition of genes involved in retaining pluripotency. SBT-1214 inhibited the majority of stem cell-related genes in all colon CSCs examined. It is worthy of note that many of these genes are related to self-renewal, regulation of symmetric/asymmetric division and pluripotency. These results provided strong support for the use of this new-generation taxoid, SBT-1214, as the highly potent cytotoxic antitumor agent component of this study against PPT2 cells and tumors.

A further improvement in taxoid drug delivery was the conjugation of taxoids to natural fatty acids (polyunsaturated fatty acids (PUFAs)). This is an attractive strategy mainly because, (a) some PUFAs possess cancer-specific toxicity via signaling pathways overexpressed in various cancers, (b) various cytotoxic drugs and PUFAS often exhibit synergistic effects against various cancer cell lines, (c) PUFAs appear to have protective effects on healthy cells by preventing drug induced apoptosis, (d) conjugation may decrease systemic toxicity by altering the pharmacokinetic properties of the cytotoxic drugs, and (e) PUFAs are FDA-approved food additives. It has been shown that n-3 PUFAs inhibits the production of carcinogenic eicosanoids derived from n-6 PUFAs through various mechanisms. Eicosanoids that are derived from n-3 PUFAs generally exhibit an inhibitory effect on inflammation and tumor growth. Finally, n-3 PUFAs have been shown to inhibit the ERK1/2 pathway which has been implicated in drug resistance. All of these factors may be contributing to the observed synergy between n-3 PUFAs and a variety of cytotoxic agents.

Among naturally occurring n-3 PUFAs, docosahexaenoic acid (DHA) exhibited the highest potency and thus has been studied extensively. It has been shown that DHA is taken up readily and preferentially by tumor cells for use a biochemical precursor and energy source. Not only does this effect produce a preferential tumor targeting effect, but DHA conjugates also show reduced efflux by Pgp. A DHA conjugate of the first-generation taxoid PX was developed (TAXOPREXIN®: Protarga/Luitpold). The DHA conjugate was found to be is voraciously taken up by tumor cells, internalized (probably through strong lipid-lipid interaction of the DHA moiety with cancer cell membrane), and slowly hydrolyzed by esterases in the cancer cell. DHA does not seem to be a good substrate for Pgp, and was found to reduce the efflux of PX.

The conjugation of DHA to first generation taxoids is not, however, an optimum strategy for overcoming MDR in CSCs and other cancer cells. If cancer cells are over expressing Pgp and/or other ABC transporters, PX molecules, even when released slowly, will be caught by the efflux pump(s) and eliminated from the cancer cells.

Because second-generation taxoids like SBT-1214 already possessed intrinsic resistance to Pgp-mediated efflux, the strategy of making conjugates possibly tumor-targeting by exploiting EPR effects of HAS-fatty acid-taxoid complexes and making tumor-selective transcytosis of HSA complex via Gp 60 by conjugating DHA to these taxoids was developed. The result was the next-generation of taxoids, which include taxoid-fatty-acid conjugates, as exemplified by DHA-SBT-1214 and LNA-SBT-1214.

DHA conjugation to SBT-1214 also provides pro-drug properties, rendering the conjugated drug 10-fold less toxic than free SBT-1214. The DHA moiety shields the taxane backbone and prevents tubulin binding. It is not until the conjugate is taken up by the cell, and the DHA moiety is cleaved by intracellular esterases, that the compound is active.

DHA-SBT-1214 was successfully synthesized and evaluated for its anti-tumor activity against both PX-sensitive and PX-resistant human tumor xenografts in SCID mice. DHA-SBT-1214 was found to cause complete regression of both PX resistant and non-resistant tumors.

The efficacy of DHA-SBT-1214 was evaluated against colon, ovarian, pancreatic and NSCL tumor xenografts in mouse models, which exhibited impressive efficacy. However, in these studies, DHA-SBT-1214 was formulated in solutol HS-15 (or polysorbate 80)/ethanol/saline, and the use of an excipient was found to impose well-documented adverse effects, ascribed to the excipient and ethanol, as well as some stability issues at lower concentration of the excipient. Therefore, Applicants have studied the efficacy of the nanoemulsion formulation, developed in a formulation research laboratory. Despite the robust pre-clinical effects seen with DHA-SBT-1214, there are drawbacks to using the current formulation and Applicants are seeking ways to potentially improve the safety, PK, distribution, retention and ease of use in the clinic.

Although clinically active, taxanes have several issues. These include poor drug solubility, serious dose-limiting toxicities such as myelosuppression, peripheral sensory neuropathy, allergic reactions, and eventual development of drug resistance. A number of these side effects have been associated with the solvents used for dilution of these antineoplastic agents: CrEL for paclitaxel and polysorbate 80 for docetaxel. In particular polyoxyethylated castor oil is biologically and pharmacologically active and leaches plasticizers from standard intravenous (i.v.) tubing releasing di(2-ethylhexyl)phthalate (DEHP). Its infusion produces histamine release with consequent well-described hypersensitivity reactions, including anaphylaxis. In early phase I trials 20% to 40% of un-premedicated patients were affected by these reactions. Moreover it has been also associated with hyperlipidemia, abnormal lipoprotein patterns, aggregation of erythrocytes, and prolonged, sometimes irreversible sensory neuropathy which may be associated with demyelination and axonal degeneration. CrEL can also cause neutropenia. In addition, reports have linked these solvents to the alterations in paclitaxel and docetaxel pharmacokinetic profiles. Hypersensitivity reactions can also occur with polysorbate 80, though to a lesser extent than with CrEL. Polysorbate 80 has also been associated with sometimes severe and irreversible sensory and motor neuropathies. Moreover polysorbate 80 can alter membrane fluidity, leading to cumulative fluid retention. This unique docetaxel toxicity may be reduced by prophylactic corticosteroids. Another important point is that CrEL and polysorbate 80 may limit tumor penetration with a negative impact on efficacy. In particular, the formation of large polar micelles of CrEL-paclitaxel in the plasma compartment entraps the drug and can lead to non-linear pharmacokinetics due to decreased drug clearance and decreased volume of distribution. This contributes to a lack of dose-dependent antitumor activity.

Because DHA-SBT-1214 is extremely hydrophobic, it needs to be formulated in polysorbate 80/ethanol/saline or Solutol H-15/ethanol/saline in order to be infused intravenously. As mentioned earlier, vehicles such as Cremophor and polysorbate 80 produce serious side effects and undesirable effects on pharmacokinetics were mentioned previously.

Nanoscale molecules possess a unique property in their use as the vehicle for anticancer drugs, because of the "enhanced permeability and retention (EPR)" effect. Since the accumulation of nanoscale molecules does not require a specific receptor, the EPR effect is passive in nature, but has been demonstrated to be efficacious. Since the nanoemulsion formulation protocol includes phospholipids and fish oil, the use of DHA-SBT-1214 has a clear advantage over SBT-1214 itself for high affinity to the fish oil component and thus high efficiency in encapsulation, achieving high concentration of the drug inside micelles.

The first line therapy for castration-resistant prostate cancer (CRPS) has been docetaxel with prednisone, and cabazitaxel has been approved by FDA in 2010 in place of or in addition to docetaxel treatment. However, CRPS involving CSCs does not exhibit androgen signaling and thus this type of CRPS is not responding to the combination of docetaxel or cabazitaxel with prednisone.

There is a great need for delivery systems that enhance the solubility, MDR resistance properties, and CSC targeting of PUFA-taxoid conjugates such as DHA-SBT-1214, as well as methods of treating prostate cancer.

SUMMARY OF THE INVENTION

The present invention provides a composition including an omega-3 polyunsaturated fatty acid (PUFA)-taxoid conjugate encapsulated in an oil-in-water nanoemulsion (NE) drug delivery system.

The present invention also provides a pharmaceutical composition including a PUFA-taxoid conjugate encapsulated in an oil-in-water NE drug delivery system.

The present invention further provides a method of treating cancer, by administering an effective amount of a pharmaceutical composition including a PUFA-taxoid conjugate encapsulated in an oil-in-water NE drug delivery system to a subject in need of treatment, and treating cancer.

The present invention still further provides a method of overcoming multidrug resistance by exposing a multidrug resistant cell to an effective amount of a pharmaceutical composition including a PUFA-taxoid conjugate encapsulated in an oil-in-water NE drug delivery system, and inducing the death of the multidrug resistant cell.

The present invention also provides a method of eliminating a cancer stem cell, by exposing a cancer stem cell to an effective amount of a pharmaceutical composition including a PUFA-taxoid conjugate encapsulated in an oil-in-water NE drug delivery system, and inducing the death of the cancer stem cell.

The present invention further provides a method of reducing the stemness of a cancer stem cell, by exposing a cancer stem cells to an effective amount of a pharmaceutical composition including a PUFA-taxoid conjugate encapsulated in an oil-in-water NE drug delivery system, and reducing the expression of stemness-promoting genes in the cancer stem cell.

The present invention provides for a method of increasing retention times of a PUFA-taxoid conjugate in the body of a subject, by administering an effective amount of a pharmaceutical composition including a PUFA-taxoid conjugate encapsulated in an NE drug delivery system, and retaining the pharmaceutical composition in the body for a longer period of time than a solution form of the pharmaceutical composition.

The present invention also provides for a method of providing a slower release profile of a PUFA-taxoid conjugate in the body of a subject, including the steps of administering an effective amount of a pharmaceutical composition including a PUFA-taxoid conjugate encapsulated in an NE drug delivery system, and releasing the pharmaceutical composition in the body at least three times slower than a solution form of the pharmaceutical composition.

BRIEF DESCRIPTION OF THE DRAWINGS

Other advantages of the present invention are readily appreciated as the same becomes better understood by reference to the following detailed description when considered in connection with the accompanying drawings wherein:

FIG. 9A is a graph of the percentage maximal response as a function of DHA-SBT-1214 when administered in aqueous solution or in nanoemulsion formulations to PPT2 cells, and FIGS. 9B-9G are photographs of PPT2 spheroids treated with different concentrations of DHA-SBT-1214 nanoemulsions and observed under microscope for toxicity (control (FIG. 9B)), 10 nM (FIG. 9C), 100 nM (FIG. 9D), 1 μM (FIG. 9E), 5 μM (FIG. 9F), and 10 μM (FIG. 9G);

FIGS. 11A-11F are photographs of mice tumors (FIG. 11A shows control tumors from mice treated with vehicle, FIGS. 11B and 11C show tumors from Abraxane treated mice (25 and 40 mg/kg, respectively), FIGS. 11D, 11E, and 11F show tumors from NE-DHA-SBT treated mice (25, 30 and 40 mg/kg, respectively)), FIG. 11G is a graph of body weight alterations induced by treatment with different concentrations of NE-DHA-SBT.

FIG. 13B-13D—30 mg/kg NE-DHA-SBT-1214 treated tumor show massive hyalurization, vacuolization and extensive necrosis. Tissues form control untreated mice: FIG. 13E—liver; FIG. 13G—intestine; FIG. 13I—kidney; FIG. 13K—pancreas; tissues from 40 mg/kg NE-DHA-SBT treated mice: FIG. 13F—liver (×40 in insert); FIG. 13H—intestine; FIG. 13J—kidney; and FIG. 13L—pancreas;

FIG. 14A is a photograph of floating spheroids and compact holoclones under detached spheroids, and FIG. 14B is a photograph of floating spheroids produced by primary cell suspension from control (untreated) tumor;

FIG. 15A is a photograph of single spheroid and absence of adherent colonies or viable cells, and FIG. 15B is a photograph of single spheroid in cultures induced by tumor cells treated with N E-DHA-SBT-1214;

FIG. 16 is a graph of post-treatment cell viability analysis in residual tumors after culturing in spheroids in untreated control spheroids;

FIG. 17 is a graph of post-treatment cell viability analysis in NE-DHA-SBT-1214 treated spheroids;

FIG. 19A is a graph of stability, FIG. 19B is a graph of particle size, FIG. 19C is a graph of polydispersity index, and FIG. 19D is a graph of zeta potential;

DETAILED DESCRIPTION OF THE INVENTION

Figure 1:
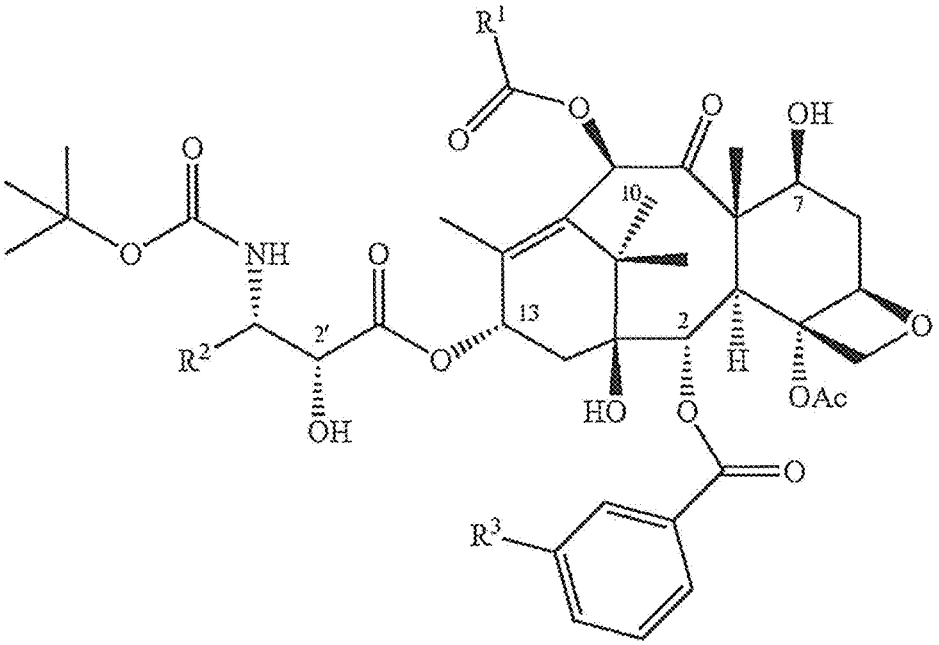
FIG. 1 shows a chemical structure of the PUFA-taxoid conjugate DHA-SBT-1214.

The present invention includes an omega-3 polyunsaturated fatty acid (PUFA)-taxoid conjugate formulated in an oil-in-water nanoemulsion (NE) drug delivery system. The preferred embodiment is NE-DHA-SBT-1214, in which the PUFA-taxoid conjugate is DHA-SBT-1214, whose structure is shown in FIG. 1.

The term "second-generation taxoid" will be used to refer to a first-generation taxanes, such as paclitaxel (taxol) and docetaxel (taxoid), in which (i) the C-3'-phenyl group is replaced with an alkenyl or alkyl group and (ii) the C-10 position is modified with certain acyl groups, and a C-3'N position is a t-Boc group. The term "PUFA-taxoid conjugate" will be used to refer to a second generation taxoid with a modified C2-benzoyl group at its meta position. PUFA-taxoid conjugates are characterized by their ability to virtually circumvent the Pgp-mediated MDR (Ojima I. and Das M., Recent advances in the chemistry and biology of new generation taxoids. J Nat Prod. (2009) 72(3): 554-565).

The term "nanoemulsion" (NE) will be used to refer to an oil-in-water emulsion with mean droplet diameters ranging from 50 to 1000 nm, with a diameter of >200 nm being preferred. The preferred NE oil phase is prepared as in U.S. Patent Application Publication US20070148194 to Amiji, et al. using omega-3 fatty acid-rich edible oils, such as fish oil or flax-seed oil. Other oils can be used such as, but not limited to, pine nut oil, safflower oil, primrose oil, black currant oil, borage oil, wheat germ oil, chia oil, hemp oil, perilla oil, grape oil, squalene oil, and fungal oil. The oil droplet is modified with surfactants, including phospholipids (e.g., LIPOID®) and poly(ethylene oxide)-containing non-ionic surfactants (e.g., Pluronic or Tween). The surface of the oil droplet can also be modified for selective targeting to tumor cells with a targeting agent, including the use of folate, EGFR peptide, and other known targeting ligands. The composition can also contain image contrast agents, including fluorophores, MRI contrast agents, or radioactive compounds.

The PUFA in the conjugate is preferably DHA (C-22), but can also be eicosapentaenoic acid (EPA, C-20), or alpha-linolenic acid (LNA, C-18).

Figure 2A:
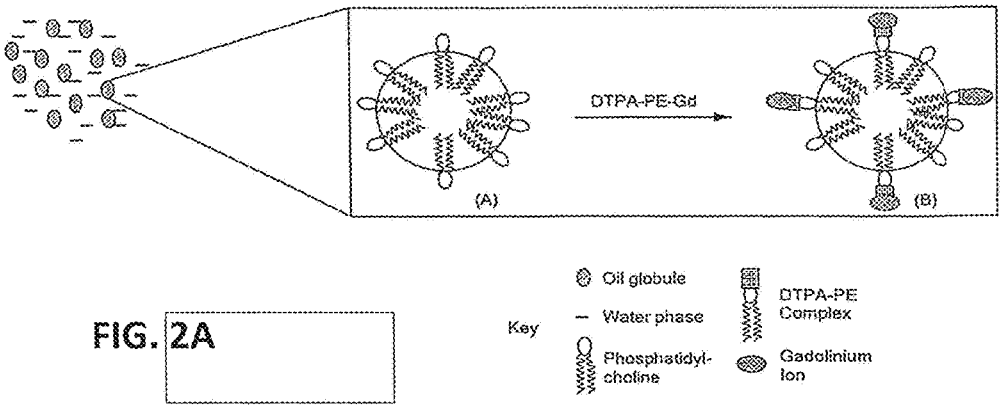
FIG. 2A shows the structure of a typical NE, and the structure of a typical nanoparticle of the NE (right-hand side), according to the present invention.
Figure 2B:
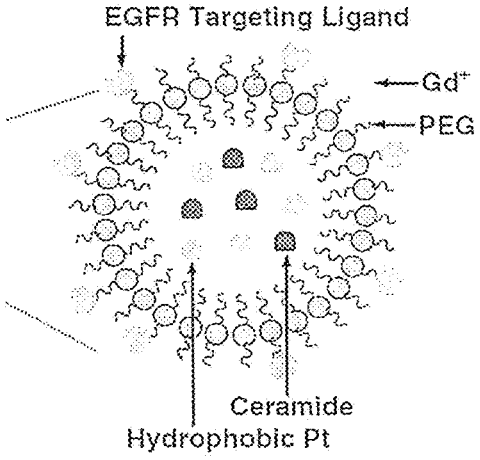
FIG. 2B shows the structure of an NE nanoparticle including a surface peptide for targeting $EGFR^+$ cells.

The present invention includes formulations of PUFA-taxoid conjugates, which are encapsulated into nanoparticles in NE as disclosed in U.S. Patent Application Publication US20070148194 (2007) to Amiji, et al., which is incorporated herein in its entirety. The structure of a typical NE is shown on the left-hand side of FIG. 2, and the structure of a typical nanoparticle of the NE is shown on the right-hand side of FIG. 2. The preferred PUFA-taxoid conjugate is DHA-SBT-1214, whose structure is shown in FIG. 1. Alternatively, any taxoid, or combination of taxoids, can be encapsulated in an NE, including, but limited to, any of the PUFA-taxoid conjugates described in U.S. Pat. No. 7,820,839, to Ojima, et al., and in Ojima I and Das M, (2009), both of which are incorporated herein in their entirety. Details of formulation are provided herein, in EXAMPLE 3.

Figure 4A:
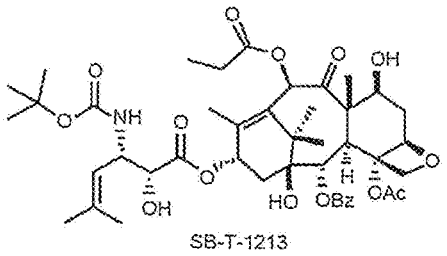
FIG. 4A shows a chemical structure of SBT-1213.
Figure 4B:
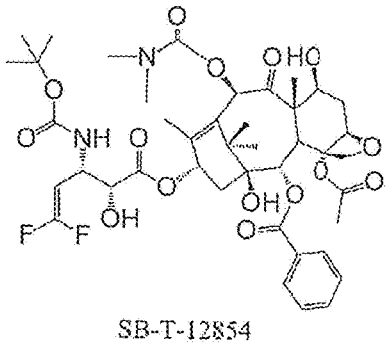
FIG. 4B shows a chemical structure of SBT-12854.
Figure 4C:
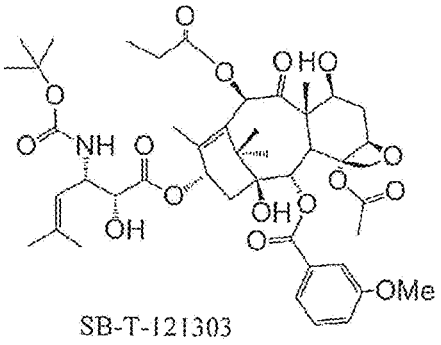
FIG. 4C shows a chemical structure of SBT-121303.
Figure 4D:
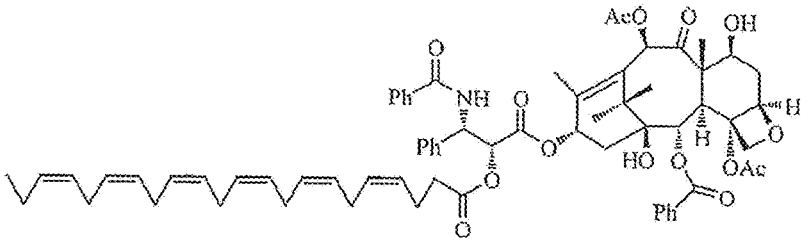
FIG. 4D shows a chemical structure of DHA-Paclitaxel.

Other taxoids which can be included in the present invention, as NE formulations include, but are not limited to, paclitaxel, docetaxel, SBT-1213 (FIG. 4A), SBT-12854 (FIG. 4B), and SBT-121303 (FIG. 4C) (Matesanz, et al., 2014); SBT-1216, SBT-11033, SBT-121313, SBT-121602 (Ojima, et al., 2009), cabazitaxel, SBT-1212, SBT-1217, SBT-1102, SBT-1103, SBT-1104, SBT-1106, SBT-1107, SBT-121301, SBT-121302, SBT-121304, SBT-121403, SBT-11031, SBT-11032, SBT-11034, SBT-12851, SBT-12852, SBT-12853, SBT-12855, SBT-12851-1, SBT-12851-3, SBT-12852-1, SBT-12852-3, SBT-12853-1, SBT-12853-3, SBT-12854-1, SBT-12854-3, SBT-12855-1, and SBT-12855-3. Also included are PUFA-conjugated second generation taxoids, including, but not limited to, DHA-paclitaxel (FIG. 4D) (Bradley, et al., 2001); DHA-docetaxel, DHA-SBT-1213, DHA-SBT-1103, DHA-SBT-1104, DHA-SBT-1216, LNA-SBT-1213, LNA-paclitaxel, LNA-docetaxel, DHA-cabazitaxel, and LNA-cabazitaxel, where LNA=α-linolenic acid. Also, DHA or LNA esters of any of the above second-generation toxoids can be used. One skilled in the art can easily make such esters. Working examples of their formulation and effectiveness are found within the indicated references, which are incorporated in their entirety herein.

An exemplary PUFA-taxoid conjugate is DHA-SBT-1214. The advantages of DHA-SBT-1214, as previously discussed, include effectiveness at targeting cancer cells, including CSCs, and at overcoming MDR. More detailed evidence of the effectiveness of DHA-SBT-1214 in overcoming drug resistance in is given herein in EXAMPLE 1. In these experiments, DHA-SBT-1214 was effective against SCID mouse xenografts of paclitaxel (PX)-resistant human cell lines DLD1 (colon cancer), PANC-1 and CFPAC-1 (pancreatic cancer), and H460 (non-small cell lung cancer). In addition, there is evidence that DHA-SBT-1214 has special actions on CSCs. First, the parent drug, SBT-1214, reduces the "stemness" of CSCs, that is, reduces the expression of stemness-promoting genes and transcription factors, including those key to pluripotency, such as Sox-2, Oct3/4, c-Myc, Klf4 and others (Botchkina et al., 2010 & 2013, and EXAMPLE 2). This reduces or eliminates the CSC component of a tumor, rendering the tumor more susceptible to therapy. Details of the experiments are provided herein, in EXAMPLE 2. In addition, SBT-1214 has been shown to polymerize tubulin in a matter of minutes, as opposed to hours for PX. This rapid disruption of microtubule biology can induce cell death even in quiescent CSC.

The main drawback of DHA-SBT-1214, poor solubility in body fluids, is overcome by encapsulation in a NE formulation according to the present invention. DHA-SBT-1214 and other PUFA-taxoid conjugates can be solubilized and delivered by formulation with NEs according to the present invention. These NEs are simple colloidal carriers formed by dispersion of omega-3, -6, and -9 polyunsaturated fatty acid (PUFA) rich oils in water, and stabilized with an amphiphilic phospholipid monolayer. The NEs have a hydrodynamic diameter of <200 nm, can incorporate considerable amounts of hydrophobic drugs in the high volume fraction of the oil phase, and are suitable for delivery of poorly water soluble drugs. The NE's are composed entirely of generally regarded as safe grade (GRAS) materials, which have highly favorable safety profiles. This is a significant advantage for clinical adoption.

In previous studies using PX, the PX encapsulation efficiency of the NEs was 100%. This high drug encapsulation efficiency was attributed to the high lipophilicity of the PX, with the drug being retained in the oil core of the NE nanoparticles. NE formulations of PX were stable during a 3-month storage period, with no phase separation or change in droplet size being observed.

The NE compositions of the present invention have been found to be physically stable at 4° C. for up to 6 months, as described in Example 6. Particle size was found to be consistent during this time, and PDI and zeta potential were also analyzed. The NE compositions have increased retention times in the body compared to a solution form of the PUFA-taxoid conjugate, as detailed in Example 5. The NE composition also provides a release profile that is at least three times slower in the body than a solution form of the PUFA-taxoid conjugate, as detailed in Example 8.

Additionally, NEs composed of oils rich in omega-3 PUFA were found to enhance the PX accumulation in SKOV3 cells. NEs containing pine nut oil or flax-seed oil have 40% or 47% omega-3 PUFA respectively and have been shown to enhance the bioavailability and efficacy of PX formulations as evaluated in mice.

Another advantage of NEs is that their surfaces can be modified with targeting molecules to increase the tumor-specific delivery of encapsulated drugs. For example, NE nanoparticles bearing EGFR-binding peptide were taken up more rapidly than non-targeted NE nanoparticles by $EGFR^+$ SKOV cells. They also showed greater accumulation at 60 minutes than non-targeted NE nanoparticles. The structure of an exemplary targeted NE nanoparticle is shown in FIG.

2B. The present invention includes any suitable NE taxoid formulation wherein the NE nanoparticles bear targeting molecules, such as growth factor receptor binding peptides, monoclonal antibodies, and fragments thereof.

A particular advantage of an NE-DHA-SBT-1214 formulation is that the DHA moiety facilitates incorporation into the oil-rich nanoemulsion. The hydrophobic fatty acid tail allows for encapsulation of these pro-drugs into the lipidic core of long-circulating targeted NE.

Another advantage of NE-DHA-SBT-1214 formulations is solubility in aqueous solutions, such as injectable saline. Formulations according to the present invention therefore eliminate the need for toxic solvents, such as CREMOPHOR®. Thus, the present invention provides a PUFA-taxoid conjugate encapsulated in an oil-in-water nanoemulsion drug delivery system.

NE-DHA-SBT-1214 provides all of the advantages of DHA-SBT-1214 in a more effective and less toxic form than the unformulated parent compound. As previously discussed, these advantages of DHA-SBT-1214 include the ability to kill MDR-resistant cancer cells, including CSC, and the ability to target CSC, both by reducing the expression of stemness-promoting genes, and by killing quiescent cells, through rapid polymerization of microtubules. According to clinical precedent de-bulking of a tumor by chemotherapy causes a normally quiescent CSC population to "wake up" and repopulate the tumor cell population. It is therefore predicted that an initial treatment of NE-DHA-SBT-1214 would begin to debulk a tumor through a standard microtubule stabilizing mechanism, and also alter the gene expression profile in the CSC population. Once the CSCs begin to repopulate the tumor, they will be more susceptible to the microtubule stabilizing effects. Additionally, DHA-SBT-1214 has been shown to down-regulate CSC gene expression and cause differentiation of the CSCs whereupon they are more susceptible to DHA-SBT-1214 induced apoptosis.

Therefore, the present invention provides a method of treating cancer, by administering an effective amount of a pharmaceutical composition including a PUFA-taxoid conjugate encapsulated in an NE drug delivery system to a subject in need of treatment, and treating cancer. The cancer or CSCs being treated in the methods herein can be any type of cancer, such as, but not limited to, breast, ovary, lung, head and neck, colon, rectal, pancreatic, melanoma, brain, prostate, leukemia, sarcomas, thyroid, Non-Hodgkin Lymphoma, bladder, gliomas, endometrial, and renal cancer. The PUFA-taxoid conjugate can be any of those described herein, and especially DHA-SBT-1214. Because the PUFA-taxoid conjugate is encapsulated in the NE, it is actively taken up by the body and DHA is cleaved more efficiently than in normal delivery methods. The method can further include the step of reducing the expression of stemness-promoting genes and transcription factors in CSCs, including those key to pluripotency, such as Sox-2, Oct3/4, c-Myc, and Klf4. The stemness-promoting genes that are down-regulated can be, but are not limited to, ABCG2, ACAN, ACTB, AIN1, ALDH1A1, ALPI, ASCL2, BMP1, BMP3, CCND1, CD3D, CD4, CD8A, CD8B, CD8B1, CDH2, COL1A1, COL2A1, COL9A1, CTNNA1, DHH, DLL1, DLL3, DTX1, DVL1, FGF1, FGF3, FGFR1, FZD1, GDF2, GDF3, GJA1, GJB1, IGF1, ISL1, JAG1, KRT15, MME, MSX1, MYOD, NEUROG2, NCAM1, NOTCH1, NUMB, PARD6A, PPARD, RB1, RPL13A, S100B, SOX1, SOX2, TERT and combinations thereof. The expression of CDX2, DLX2, DNMT3B, EGR, FOXP3, GLI2, HOX family TFs, IRX4, JUN, KLF2, NFATC1, NR2F2, PCNA, PITX3, POU4F1, SIX2, SOX9, and WT1 can also be down-regulated. The method can further include the steps of reducing or eliminating the CSC component of a tumor and rendering the tumor more susceptible to therapy. The method can further include the steps of rapidly polymerizing tubulin and inducing cell death. As shown in Example 4, a nanoemulsion of DHA-SBT-1214 conjugate induces superior tumor regression and tumor growth inhibition in prostate cancer models. The composition and method can be particularly effective against paclitaxel-sensitive and paclitaxel-resistant tumors. The composition can suppress tumor growth and induce tumor shrinkage, prevent production of adherent holoclones, and prevent vascularization of the tumor. There is tumor-specific accumulation of the composition through gp60-mediated transcytosis into the tumor interstitium due to higher affinity of DHA conjugated drug to human serum albumin (HAS) which is the primary carrier for PUFAs in the bloodstream (as described in Example 4). Further, as evidenced by Example 5, the method can further include the step of retaining the pharmaceutical composition in the body for a longer period of time than a solution form of the pharmaceutical composition, and especially retaining the pharmaceutical composition at the tumor for longer periods of time.

Also, a non-conjugated version of the PUFA-taxoid can be administered along with the conjugate in any of the methods herein. Since DHA needs to be cleaved before becoming active in the body, a non-conjugated version can provide an immediate effect while the conjugated version can provide a sustained effect within the body. With especially aggressive tumors, it is desired to treat them quickly but also it is desired to have a sustained, longer effect on cancer stem cells. The combination treatment can be administered as a loading dose and a maintenance dose in a single dose or injection.

The present invention also provides a method of overcoming multidrug resistance by exposing a multidrug resistant cell to an effective amount of a pharmaceutical composition including PUFA-taxoid conjugate encapsulated in an NE drug delivery system, and inducing the death of the multidrug resistant cell. The PUFA-taxoid conjugate can be any of those described herein, and especially DHA-SBT-1214. For example, in Example 1, DHA-SBT-1214 caused complete regression of multidrug resistant tumors in mice. The method can further include the step of reducing the expression of stemness-promoting genes and transcription factors in CSCs, including those key to pluripotency, such as Sox-2, Oct3/4, c-Myc, and Klf4. The method can further include the step of reducing or eliminating the CSC component of a tumor, rendering the tumor more susceptible to therapy. The method can further include the step of rapidly polymerizing tubulin and inducing cell death.

The present invention also provides a method of eliminating a cancer stem cell, by exposing a cancer stem cell to an effective amount of a pharmaceutical composition including a PUFA-taxoid conjugate encapsulated in an NE drug delivery system, and inducing the death of the cancer stem cell. The PUFA-taxoid conjugate can be any of those described herein, and especially DHA-SBT-1214. The method can further include the step of reducing the expression of stemness-promoting genes and transcription factors in CSCs, including those key to pluripotency, such as Sox-2, Oct3/4, c-Myc, and Klf4. The method can further include the step of reducing or eliminating the CSC component of a tumor, rendering the tumor more susceptible to therapy. The method can further include the step of rapidly polymerizing tubulin and inducing cell death.

Also provided by the present invention is a method of reducing the stemness of a cancer stem cell, by exposing cancer stem cells to an effective amount of a pharmaceutical composition including a PUFA-taxoid conjugate encapsulated in an NE drug delivery system, and reducing the expression of stemness-promoting genes in the cancer stem cell. The PUFA-taxoid conjugate can be any of those described herein, and especially DHA-SBT-1214. The method can further include the step of reducing the expression of stemness-promoting genes and transcription factors in CSCs, including those key to pluripotency, such as Sox-2, Oct3/4, c-Myc, and Klf4. The method can further include the step of reducing or eliminating the CSC component of a tumor, rendering the tumor more susceptible to therapy. The method can further include the step of rapidly polymerizing tubulin and inducing cell death.

The present invention further provides for a method of increasing retention times of a PUFA-taxoid conjugate in the body of a subject, by administering an effective amount of a pharmaceutical composition including a PUFA-taxoid conjugate encapsulated in an NE drug delivery system, and retaining the pharmaceutical composition in the body for a longer period of time than a solution form of the pharmaceutical composition. As evidenced by Example 5, the NE drug delivery system for the PUFA-taxoid conjugates is able to provide longer retention times in the body as compared to a solution form, especially in the plasma and tumors. The PUFA-taxoid conjugate can be any of those described herein, and especially DHA-SBT-1214. Due to the increased retention times, lower doses of the PUFA-taxoid conjugate can also be given, thus reducing side effects.

The present invention also provides for a method of providing a slower release profile of a PUFA-taxoid conjugate in the body of a subject, including the steps of administering an effective amount of a pharmaceutical composition including a PUFA-taxoid conjugate encapsulated in an NE drug delivery system, and releasing the pharmaceutical composition in the body at least three times slower than a solution form of the pharmaceutical composition. As evidenced by Example 8, the NE compositions have a three times slower release profile than the solution form. The PUFA-taxoid conjugate can be any of those described herein, and especially DHA-SBT-1214. Due to the slower release profile, lower doses of the PUFA-taxoid conjugate can also be given, thus reducing side effects.

A pharmaceutical composition according to the present invention is preferably an aqueous solution, such as normal (0.9%) sterile, pyrogen-free saline. Less preferably, alternative solvents can be employed or carriers can be employed. The present invention can also include a compatible, pharmaceutically acceptable excipient, buffer, or stabilizer.

An "effective amount" of the pharmaceutical composition is determined by the responsible manufactures and/or practitioners, and typically takes account of the disorder to be treated, the condition of the subject patient, the site of delivery, the method of administration and other factors. Examples of the techniques and protocols to determine effective amount can be found in Remington's Pharmaceutical Sciences, 17th ed., Gennaro, A. R. (ed.), Mack Publishing Co., Easton, Pa. 1985. In general, "an effective amount" of the composition is defined as an amount that is sufficient to significantly induce a positive modification of a disease state. The term also implies that the amount is small enough to avoid serious side-effects. The determination of these amounts typically lies within the scope of sensible medical judgment. An "effective amount" a will vary according to the particular condition to be treated and also with the age and physical condition of the patient to be treated, the severity of the condition, the duration of the treatment, the nature of the accompanying therapy, of the particular pharmaceutically acceptable carrier used, and similar factors. The pharmaceutical compositions according to the present invention can be used for both human and veterinary medical purposes.

The pharmaceutical compositions of the present invention are preferably administered parenterally, most preferably by an intravenous route, but can alternatively be administered by intramuscular, subcutaneous, intradermal, intrathecal, and epidural routes. For specific purposes, such as tumor-localized treatments, administration can also be via non-parenteral routes, such as oral, sublingual, topical, transdermal, ophthalmic, otic, nasal, rectal, and vaginal routes.

Various embodiments and aspects of the present invention, as delineated previously, find experimental support in the following examples.

Example 1: The Parent PUFA-Taxoid Conjugate, DHA-SBT-1214, is Effective Against Both PX-Sensitive and PX-Resistant Tumors In Vivo Effect of DHA-SBT-1214 on Growth of PX-Resistant Human Colon Cancer Xenografts in SCID Mice.

Figure 3A:
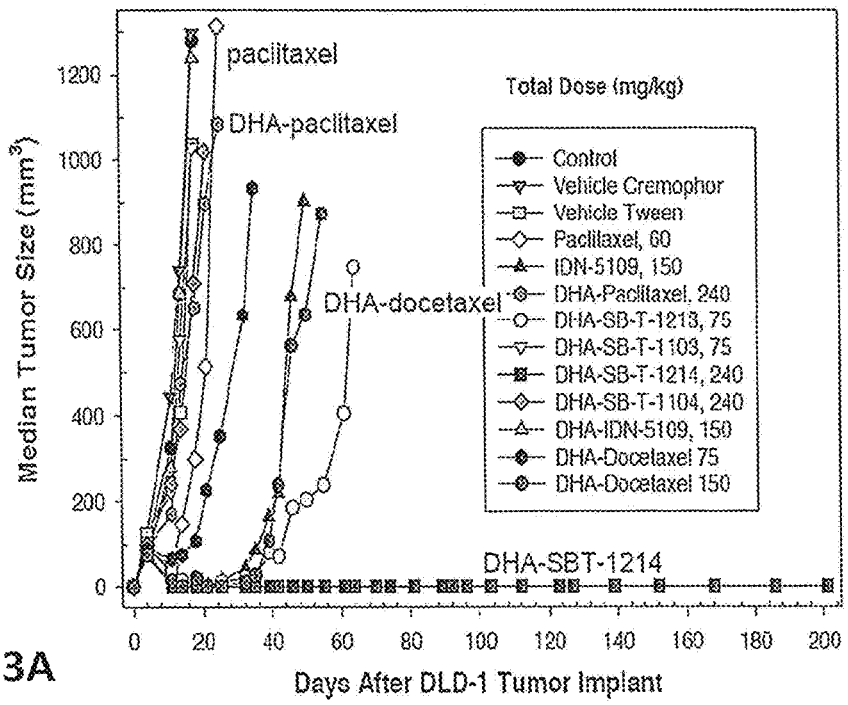
FIG. 3A shows a graph of the growth of $Pgp^+$, PX-resistant DLD1 colon cancer xenografts in SCID mice, under treatment with DHA-SBT-1214 and other taxoids.

In experiments using the paclitaxel-resistant, Pgp($^+$) DLD1 human colon tumor xenograft implanted s.c. in SCID mice, paclitaxel and TAXOPREXIN® were totally ineffective. In sharp contrast, DHA-SBT-1214 caused complete regression of the DLD-1 tumor in 5 of 5 mice at the 80 mg/kg dose administered on days 5, 8, and 11 (tumor growth delay>187 days) (FIG. 3A).

Effect of DHA-SBT-1214 on the Growth of Human Pancreatic Cancer Xenografts in SCID Mice.

Figure 3B:
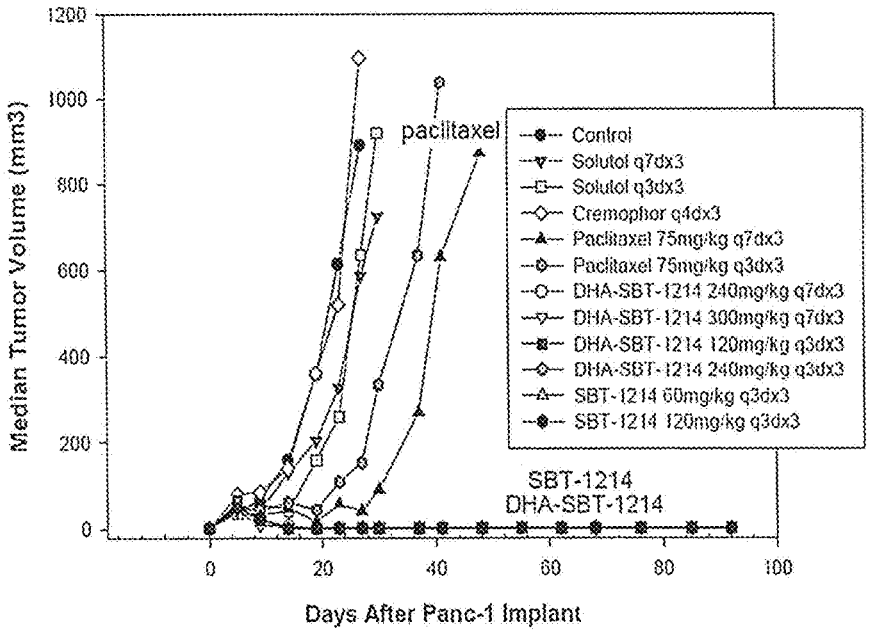
FIG. 3B shows a graph of the growth of PANC-1 pancreatic cancer xenografts in SCID mice, under treatment with DHA-SBT-1214 and other taxoids.

This experiment compared a q7dx3 with a q3dx3 schedule for PX and DHA-SBT-1214 using a human PANC-1 pancreatic tumor xenograft in RPCI SCID mice. The results (FIG. 3B) indicated that both schedules were very effective in this human pancreatic tumor xenograft (tumor growth delay>90 days). The maximum tolerated does (MTD) for DHA-SBT-1214 appeared to be 240 mg/kg total dosage (80 mg/kg×3 inj=240 mg/kg), with one toxic death occurring at the 300 mg/kg total dose. All mice that received DHA-SBT-1214 achieved complete remissions, and essentially were cured. In contrast, PX was only weakly effective, showing tumor growth delays of 18 days with q7dx3 schedule and 13 days with q3dx3 schedule and no complete remissions.

Effect of DHA-SBT-1214 on the Growth of Human Pancreatic Adenocarcinoma Xenografts in SCID Mice.

Figure 3C:
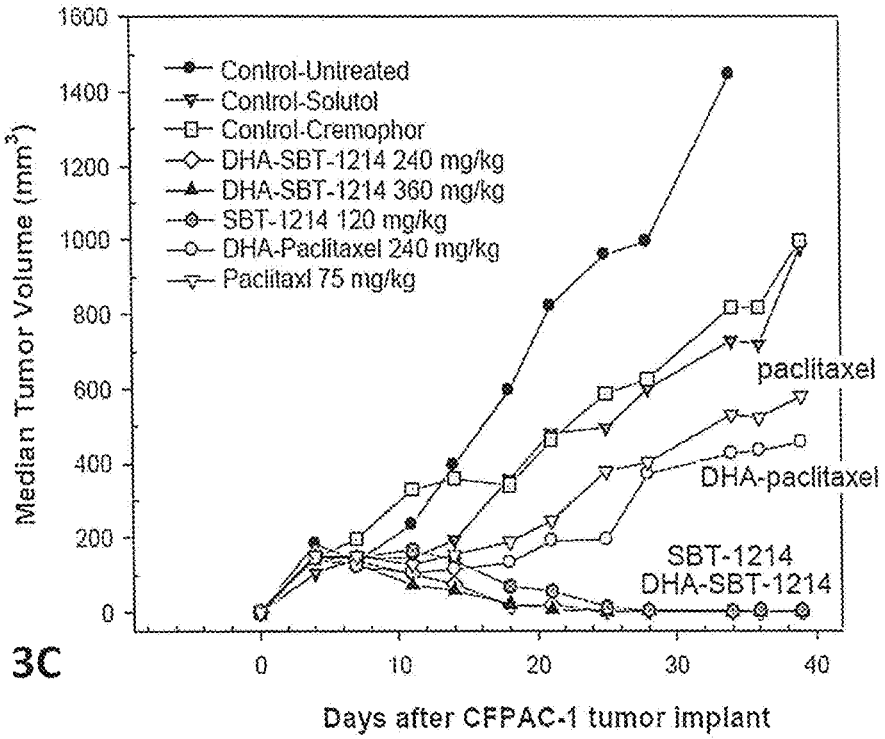
FIG. 3C shows a graph of the growth of CFPAC-1 pancreatic adenocarcinoma xenografts in SCID mice, under treatment with DHA-SBT-1214 and other taxoids.
Figure 3D:
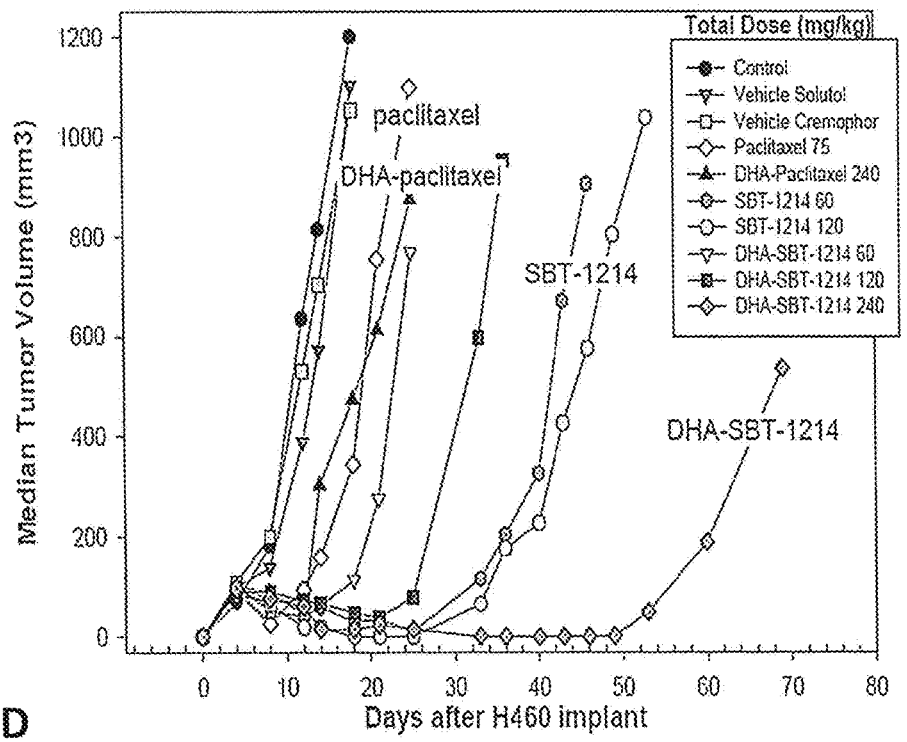
FIG. 3D shows a graph of the growth of H460 non-small cell lung tumor xenografts in SCID mice, under treatment with DHA-SBT-1214 and other taxoids.

This experiment compared the efficacy of PX, DHA-paclitaxel and DHA-SBT-1214 using a human CFPAC-1 ductal pancreatic adenocarcinoma xenograft. DHA-SBT-1214 at a 240 mg/kg or 300 mg/kg total dose was very effective, causing complete regression and cure for 5 in 5 or 4 in 4, respectively (FIG. 3C). PX and DHA-paclitaxel were much less effective with only minor tumor growth delay as compared to vehicles. SBT-1214 (120 mg/kg total dose) exhibited results superior to PX, with tumor regressions for 6 in 6 mice although only 1 in 6 was cured, and the drug appeared to be more toxic than DHA-SBT-1214. SBT-1214-treated mice showed only minor weight loss (<4%) until day 20, while the weight loss was negligible for DHA-SBT-1214-treated mice, at either the 240 mg/kg or 300 mg/kg total dose.

Effect of DHA-SBT-1214 on the Growth of Human Non-Small Cell Lung Cancer Xenografts in SCID Mice.

This experiment compared DHA-SBT-1214, PX, DHA-paclitaxel and SBT-1214 against highly aggressive H460 human non-small cell lung tumor xenograft. Only minor tumor growth delays were seen with PX at the MTD (75 mg/kg total dose) and DHA-paclitaxel at MTD (240 mg/kg total dose), at 8 and 3 days, respectively. In contrast, DHA-SBT-1214 and SBT-1214 caused tumor growth delays of 55 and 34 days at about MTD (240 mg/kg and 120 mg/kg total dose, respectively). DHA-SBT-1214 was clearly better tolerated than SBT-1214.

The results of this Example show that DHA-SBT-1214, the parent of NE-DHA-SBT-1215, is effective at overcoming MDR in a variety of target cells. These results indicate that an NE-DHA-SBT-1214 formulation, according to the present invention, will produce anti-tumor effects at least equivalent to those of DHA-SBT-1214, in a preparation that is more soluble and less toxic than the unformulated parent compound.

Example 2: The Parent Taxoid SBT-1214 Reduces the Stem Cell Properties of Cancer Stem Cells Experiments were carried out with a patient-derived cancer stem cell line for prostate cancer, PPT2 (Botchkina 2013, Rowehl 2014). The cell line PPT2 was generated from a patient-derived prostate cancer tumor. Subcloning of these small-cell-containing holoclones led to dramatic enrichment of cells expressing high levels of CD133, CD44, CD44v6, EpCAM, CD49f and CD166. The PPT2 cell line was serially propagated as NOD/SCID mice tumor xenografts, floating 3D spheroids and type I collagen-adherent cultures. According to the ATCC report (ID number 002872), the PPT2 cells were unique human cells not contaminated with any known established cell lines. Although phenotype of the CSC-enriched cultures was dynamic due to the dual nature of the CSCs (i.e., ability to self-renew and to generate committed progenitors), the PPT2 cells retained a relatively stable phenotype, even up to 8 weeks after MACS-CD133$^+$ cell sorting and culturing on type I collagen coated surfaces in serum-free medium. Virtually the entire population of PPT2 cells remained undifferentiated (only 3-5% expressing a marker of differentiated cells, pan-keratin), positive for EpCAM, CD49f, and the standard isoform of CD44 (98-99%). Up to 72% expressed the variant isoform, CD44v6. After >27 passages, about 90% of PPT2 cells still expressed moderate-to high levels of CD133, and possessed very high sphere-forming capacity in 3D culture. The vast majority of the CD133$^+$ PPT2 cells expressed high cytoplasmic levels of vimentin and nestin, characteristic of neural and embryonic stem cells. Both nuclear and cytoplasmic fractions of the PPT2 cells expressed c-Myc, whereas other pluripotency markers (Oct-4 and Sox-2) were detected only in nuclear fraction. Importantly, PPT2 cells were negative for pro-apoptotic/tumor suppressor proteins, p53 and p21, and were extremely resistant to standard anticancer drugs.

To characterize possible drug induced alterations in stemness gene expression, CD133$^+$ PPT2 cells were analyzed before and after treatment with a combination of SBT-1214 and CMC 2.24, a chemically-modified curcumin. Using a PCR array assay (PAHS 501; SABiosciences) with filtering criteria of a 1.5- or greater-fold change in expression, it was found that about 50% of the analyzed 84 stem cell-related transcription factors (TFs) were upregulated in CD133$^+$ versus differentiated PrC cells. Among them were CDX2, DLX2, DNMT3B, EGR, FOXP3, GLI2, HOX family TFs, IRX4, JUN, KLF2, NFATC1, NR2F2, PCNA, PITX3, POU4F1, SIX2, SOX2, SOX9, TERT, WT1 and others. A single treatment with SB-1214 (1 μM) and CMC2.24 for 24 hours induced significant down-regulation of these over-expressed genes. Western blot analysis showed that SBT-1214 induced moderate down-regulation of c-Myc and Sox2 in nuclear extracts of both CD133$^+$ and bulk PPT2 cells. Importantly, nuclear fractions of both CD133+ and bulk PPT2 cells did not express the two tumor suppressors/regulators of apoptosis, p53 and p21, which partially can explain their extreme resistance to anti-cancer drugs. SBT-1214 induced expression of p21 and p53. Such "gene wake-up" induced by pretreatment with the drug dramatically increased further sensitivity of these highly drug resistant cells to the second treatment, leading to virtually complete death of the CSC-enriched cells.

Figure 5:
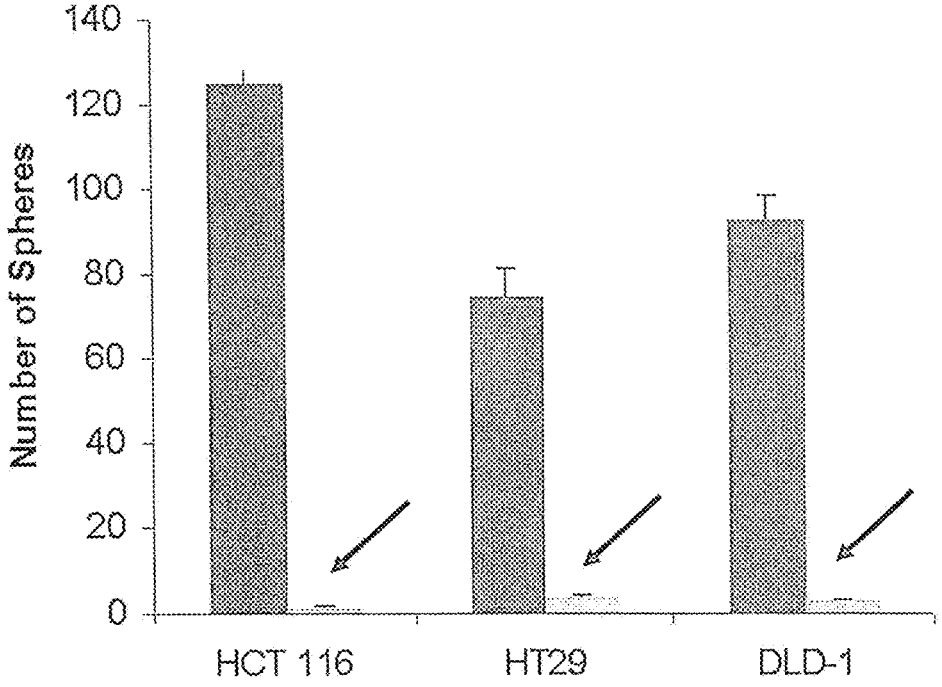
FIG. 5 shows experimental results demonstrating the cytotoxic effects of SBT-1214 upon cancer stem cell rich tumor spheroids.

In another example, stem-cell enriched populations of colon cancer cells were selected from three invasive colon cancer cell lines, HCT116, HT29, and DLD-1. The populations were grown as 3D multicellular spheroids. It was found that SBT-1214 effectively induced cytotoxicity in all three types of spheroids (FIG. 5A). Furthermore, SBT-1214 treatment downregulated the following stemness-associated genes in spheroids of all three tumor cell types:

HCT116: SOX1, RPL13A, BMP1, BMP3, NEUROG2, GJB1, GJA1, ASCL2, CTNNA1, GDF2, ALPI, S100B, CD8B1, ACTB, CCND1, FGF1, PARD6A, DVL1, GDF3, ISL1, CD3D, MME, FGFR1, RB1, AIN1, ALDH1A1, CD8A, PPARD, FZD1, NUMB and ABCG2;

HT29: ACAN, ALPI, BMP3, CD3D, CD4, CD8A, CD8B, CDH2, COL2A1, COL9A1, DHH, DLL1, DLL3, DTX1, FGF1, FGF3, FZD1, GDF2, IGF1, MME, MYOD, NCAM1, NEUROG2, S100B, SOX2, and TERT;

DLD-1: CD4, CDH2, COL1A1, DLL1, DTX1, IGF1, FGF3, FZD1, JAG1, KRT15, MSX1, NCAM1 and NOTCH1 (Botchkina, et al., 2010).

The results of these exemplary studies indicate that SBT-1214 reduces stem cell properties in CSC and effectively eliminates them. It is predictable that SBT-1214, when formulated as NE-DHA-SBT-1214 will produce similar suppression of stemness gene expression, but with greater solubility and less toxic effect, than the unformulated parent compound.

Example 3: Preparation of Formulations of NE-DHA-SBT-1214

The NEs of the present invention are simple colloidal carriers formed by dispersion of omega-3 -6 & -9 polyunsaturated fatty acid (PUFA) rich oils in water and stabilized with an amphiphilic phospholipid monolayer. Detailed descriptions of the compositions of these NEs, and methods of making them, are found in U.S. Patent Application Publication US20070148194 (2007) to Amiji, et al, NEs composed of oils rich in omega-3 PUFA have been found to enhance PX accumulation in SKOV3 cells.

Briefly, to formulate NE-DHA-SBT-1214, an oil-in-water NE formulation is prepared by a high energy microfluidization process. First, the aqueous phase is prepared by dissolving egg phosphatidylcholine and a pegylating agent (PEG2000DSPE) in deionized water. DHA-SBT-1214 is then added to PUFA rich oils to obtain the oil/lipid phase. The mixture is pre-homogenized for 5 cycles at low pressure with a MICROFLUIDIZER® processor M-110EH to form a coarse emulsion, and another 5 cycles of high pressure homogenization to form a NE with the droplet size<200 nm. The prior linkage of DHA to SBT-1214 facilitates incorporation of DHA-SBT-1214 into the nanoemulsion.

It is preferred that the oil contain at least 2% (w/w) of at least one PUFA. NEs containing pine nut oil or flax-seed oil have 40% or 47% omega-3 PUFA respectively, and are among the preferred forms, having been shown to enhance efficacy of taxoid formulations as evaluated in mice (41). Other preferred oils for NE formulation include, but are not limited to, safflower, primrose, black currant, borage, wheat germ, chia, hemp, perilla, grape, squalene and fungal oils, and omega-3 rich fish oils.

An exemplary formulation that has been found to be effective for encapsulating taxoid compounds (Ganta, et al., 2010) can be adapted for SBT-1214 as follows: SBT-1214 (e.g. 10 mg) in chloroform is added to 1.0 g of extra pure grade omega-3 fatty acid-rich flax-seed oil (Jedwards International, Quincy, Mass.) in a glass vial. Chloroform is evaporated by blowing a stream of nitrogen gas. The aqueous phase is prepared by adding 120 mg of egg yolk lecithin (Lipoid E80®, Lipoid GMBH, Ludwigshafen, Germany) and 40 mg of deoxycholic acid (Acros Organics, Parsipanny, N.J.) to 4 mL of deionized distilled water and stirred at 5000 rpm for 30 min using a SILVERSON® homogenizer to achieve complete dissolution. The oil phase and the aqueous phase are heated separately to 70-75° C. for 2 min. The aqueous phase is added gradually to the oil phase and the mixture is then ultrasonicated at 21% amplitude and 50% duty cycle using VIBRA-CELL® VC 505 ultrasound instrument (Sonics and Materials, Newtown, Conn.) for 10 min to obtain stable nanoemulsions. Particle size of the oil droplets in the nanoemulsions is measured with a dynamic light scattering method using a Brookhaven Instrument's 90Plus particle size analyzer (Holtsville, N.Y.) at a 90° fixed angle and 25° C. temperature. All the samples are diluted in deionized distilled water prior to analysis, and the average oil droplet hydrodynamic diameter is determined. Polydispersity index (PDI), a measure of the distribution of particles size in the sample is also determined. Additionally, oil droplet surface charge (zeta potential) values are determined based on the electrophoretic mobility of the oil droplets using the Brookhaven Instrument's Zeta PALS method.

The specific formulation of NE-DHA-SBT-1214 is next characterized for size, charge and morphology, to determine its stability, functionality, and capacity. Determination of encapsulation efficiency (percentage of drug retained in the oil phase as a function of amount added) in the NE-DHA-SBT-1214 formulations is determined by an ultra-filtration method using well-known centrifugal filter devices. The concentration of the drug payload is determined by ICP-MS or LC-MS. If any of these measures is found to deviate significantly from desired parameters, the oil/lipid mixture can be optimized by straightforward experimentation.

Example 4

Materials and Methods

New-generation taxoid, DHA-SBT-1214 was synthesized by Dr. Ojima's laboratory at Stony Brook University, (Stony Brook, N.Y.) or ChemMaster International, Inc. (Stony Brook, N.Y.). Extra pure omega-3 rich fish oil was purchased from Jedwards International (Quincy, Mass.), Lipoid E80 from Lipoid GMBH (Ludwigshafen, Germany), DSPE PEG2000 from Avanti Polar Lipids, Inc. (Alabaster, Ala.), Tween 80 from Sigma Chemicals, Inc. (St. Louis, Mo.), CellTiter 96 $AQ_{ueous}$ one solution cell proliferation assay kit (G3580), from Promega (Madison, Wis.), Mesenchymal stem cell growth media (MSCGM) from Lonza (Portsmouth, N.H.), LAL chromogenic endotoxin quantitation kit from Thermo Scientific (Rockford, Ill.), Microscope slides single depression concave from Amscope (Irvine, Calif.), Collagenases type II and type IV from Sigma-Aldrich, Rhodamine 123 from Sigma Aldrich (St. Louis, Mo.), Anti-human CD133/2-APC antibody (clone 293C3) from Miltenyi Biotec, CA, USA; CD166-PE antibody (clone 105902) from R&D Systems, MN, USA; CD44-FITC antibody (clone F10-44-2) from or CD44-PE antibody (clone F10-44-2) from; Invitrogen/Biosources, USA; CD44v6-FITC antibody (clone 2F10) from; R&D Systems, USA, EpCAM-FITC antibody from Biosource, CA, USA, Pan-Keratin (C11) antibody—ALEXAFLUOR® 488 from Cell Signaling and all the isotype controls antibodies were purchased from Chemicon. Penicillin, streptomycin and TrypLE were obtained from Invitrogen (Grand Island, N.Y., USA). All other reagents were purchased through Fisher Scientific.

Preparation and Characterization of the Nanoemulsion Formulations

Preparation of nanoemulsion formulations was carried out as reported recently with some modifications. Instead of a sonication method, oil-in-water nanoemulsions were prepared by microfluidic method as follow. Briefly, pre-warmed oil phase (10 ml) consisting of fish oil alone (for placebo) or with DHA-SBT-1214 was gradually added to the pre-warmed water phase (40 ml) containing egg phosphatidylcholine (Lipoid E80®) (1200 mg), polysorbate 80 (Tween80®) (0.5 ml), DSPE-PEG2000 (1,2-distearoyl-Sn-glycero-3-phosphoethanolamine-N-[amino (polyethylene glycol)-2000]) (75 mg). The resultant mixture was homogenized and the oil-water suspension was passed through the zirconia plunger of an M-110EH-30 high shear fluid processor at 10,000 psi for 4 cycles to achieve a uniform nanoemulsion formulation.

The oil-in water nanoemulsion formulation was characterized by well-established protocols in the laboratory. In summary, particle size and surface charge of water diluted nanoemulsion was measured by using the Brookhaven Instrument's 90Plus ZetaPALS particle size analyzer (Holtsville, N.Y.) and the morphology of oil droplets in the nanoemulsion formulations was visualized with transmission electron microscopy (TEM). Drug loading, encapsulation efficiency and stability were evaluated using HPLC as described previously. In short, for drug loading, the nanoemulsion was sufficiently diluted with organic (acetonitrile), and 20 μL aliquot was injected into the HPLC. For encapsulation efficiency, ultra-filtration method using centrifugal filter device (molecular weight cut-off 3,000 Daltons; Millipore, Bedford, Mass.), was used. All batches of nanoemulsions were tested for endotoxin level through Limulus Amebocyte Lysate (LAL) assay according to manufacturer's instructions before apply for both in vivo and in vitro studies.

Cell Culture, Isolation, Purification and Characterization of Tumor-Initiating Cells The human prostate cancer stem cells (PPT2), prostate adenocarcinoma CSC-enriched cell line was recently established from the stage pT2c pNX pMX prostate cancer patient. Briefly, PPT2 cells were cultured on rat collagen type1 coated tissue culture dishes as monolayer and for inducing floating 3D spheroid culture, these cells were seeded on ultra-low-adherent (ULA) plates or flasks (Corning) under 5% CO2 atmosphere at 37° C. To ensure and control reliable enrichment of CSCs, cells were labeled with several markers conjugated with different fluorescent dyes. These stained cells were either sorted and analyzed with multiparametric flow cytometer BD FACSAria (Becton Dickinson, CA) or dissociated cells were centrifuged and labeled with CD133 Abs directly or indirectly conjugated with ferromagnetic beads (Miltenyi Biotec, CA) as recommended by the manufacturer. Isolated cells were tested functionally for their ability to induce round colonies (holoclones) and 3D spheroids under non-adherent culture conditions. For cell culture from primary mouse tumors, tumor tissues were mechanically and enzymatically disaggregated into single cell suspension at sterile conditions, rinsed with Hank's balanced salt solution and incubated for 1.5 hours at 37° C. in serum-free RPMI medium 1640 containing 200 units/ml Collagenases type II and type IV, 120 μg/ml penicillin and 100 μg/ml streptomycin. Cells were further disaggregated by pipetting and serial filtration through cell dissociation sieves (size 40 and 80 meshes; Sigma-Aldrich). Primary cell suspensions were grown both as monolayer and in spheroids.

Cellular Uptake Studies

These studies were performed in order to evaluate and compare uptake of rhodamine encapsulated nanoemulsion formulation in both monolayer and spheroid cultured PPT2 cells. Fluorescence confocal microscopy studies were performed to assess the qualitative cellular internalization of the nanoparticles as described previously. Briefly cells were cultured both as monolayer and in spheroids. After obtaining acquired confluency of the cells in monolayer and optimum diameter of spheroids, these were incubated with different concentrations of the dye encapsulated nanoemulsions for 8 hours. Cells and spheroids were washed with cold phosphate buffered saline (PBS), fixed with 4% paraformaldehyde for 20 minutes, washed with cold PBS, and mounted with DAPI on regular clean glass slides in case of monolayer cell cultures and on microscope slides with single depression concave to keep shape of the spheroid intact. Digital images were captured by LSM 700® confocal microscope (Carl Zeiss, Gottingen, Germany) at 63× magnification and analyzed using the NIH Image-J software. All setting parameters for fluorescence detection and images' analyses were held constant to allow consistency in imaging of the sample for comparison.

Cell Viability Analysis

The cell viability studies were performed with both aqueous drug solution and the nanoemulsion formulations containing different concentration of DHA-SBT-1214. For this purpose, PPT2 cells were seeded into collagen coated 96-well plates at a density of 10000 cells per well. After 24 hours, DHA-SBT-1214 in different concentrations was added to the monolayer cells either in aqueous solution or in nanoemulsion formulations along with respective controls. Cells treated with media and DMSO alone (without any drugs) were used as negative control. Eight replicates were made for each test condition. Following 48 h incubation period, cell viability was determined with CellTiter assay according to manufacturer's instructions. The absorbance of the plate was read at a wavelength of 570 nm using a BioTek-HT UV-Vis/fluorescence microplate reader. The percent cell viability was calculated based on the absorbance of the drug treated cells over the absorbance of control (media alone) cells and multiplied by one hundred. 50% inhibition of cell viability (IC50) produced by DHA-SBT-1214 in either solution or nanoemulsion formulation were calculated using Graph Pad Prism.

Mice Tumor Xenografts

All experiments involving the use of animals were carried out in strict accordance with the recommendations in the Guide for the Care and Use of Laboratory Animals of the National Institutes of Health, via a research protocol that was approved by Stony Brook University Institutional Animal Care and Use Committee (IACUC) as described previously. Briefly, after sufficient propagation, clonogenic cells expressing high levels of CD133, CD44, CD44v6, CD166 and EpCAM were resuspended in 1:1 MSCGM/Matrigel and injected to the flanks of 6 weeks old NOD/SCID mice (up to 1 million cells per mice; subcutaneously). Tumor development was monitored weekly. The primary tumor sizes were measured with a caliper on a weekly basis and approximate tumor weights determined using the formula $0.5ab^2$, where b is the smaller of the two perpendicular diameters.

In Vivo Efficacy of NE-DHA-SBT-1214 and ABRAXANE® and Ex Vivo Characterization of Primary Tumor Cells The NE-DHA-SBT-1214 (1, 3, 10, 25, 30, 40, 50 and 70 mg/kg) and ABRAXANE® (protein-bound paclitaxel, Celgene) (and 30 and 40 mg/kg) was administered intravenously; weekly, for 3 weeks to NOD/SCID mice bearing palpable tumor xenografts. Treatment was started one week after transplantation of the PPT2 cells when tumor xenografts reached approximately 50-150 $mm^3$. Systemic toxicity in NOD/SCID mice was closely monitored and evaluated by standard criteria (motor activity, morbidity, appetite, posture and appearance) and were humanely euthanized after they seemed moribund, or had too large or ulcerated tumors. After the last treatment, tumor development was monitored for an additional 4 weeks. All mice were terminated after four weeks of follow up. Some control or post-treatment residual tumors were harvested and analyzed histopathologically, for ex vivo clonogenic and sphere-forming capacities and other assays. For post treatment characterization, mouse tumor xenografts were harvested and disaggregated mechanically and enzymatically into single cell suspensions. The ability of these primary cells to induce round colonies (holoclones) and sphere formation was determined for both control (untreated) and drug treated mice. For holoclones, cells were counted and plated on 48-well plates at a final count of 300 cells per well and for sphere formation, cells were resuspended in 1:4 Matrigel/MSGM and known cell numbers were plated on ULA plates. One week after initiation, the plates were inspected for colony growth and floating sphere growth respectively. Colonies and floating sphere within each well was observed by phase contrast microscopy. Some cells from both untreated in treated tumor xenografts were used for analysis of the drug induced alterations in expression of the stem cell markers with FACS and arrays.

Statistical Data Analysis

The in vivo responses to drug treatment were evaluated as changes in tumor volume of drug treated versus untreated control xenografts. Data were expressed as means±SD for control and drug treated tumors. The statistical significance of differences was determined using Student's t-test with Graph Pad Prism® software (GraphPad Software, La Jolla, Calif., USA). The parameters used were the two-tailed distribution and the paired test. $P<0.05$ was considered statistically significant.

Results

Characterization of DHA-SBT-1214 Nanoemulsion Formulation

Nanoemulsions are heterogeneous dispersions of liquid which can either be made as oil-in-water or water-in oil order and the particle size is on the 100-150 nm scale. Nanoemulsion formulations are the most commonly used carriers for hydrophobic drug delivery, due to their effective therapeutic ability both in vitro and in vivo. Many anticancer drug encapsulated nanoemulsions have shown enhanced efficacy due to their target-specific systemic delivery to tumor site. This delivery approach has also shown enhanced therapeutic potential in our previous studies.

Figure 6A:
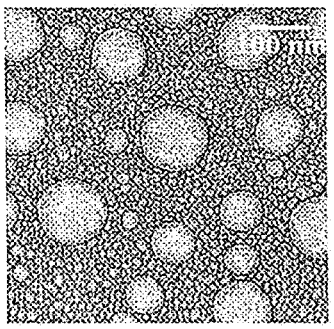
FIGS. 6A-6C are transmission electron micrographs (TEM) of the placebo (NE-Placebo) (FIG. 6A), DHA-SBT-1214 nanoemulsion formulation (NE-DHA-SBT-1214) (FIG. 6B), and ABRAXANE® (FIG. 6C)
Figure 6B:
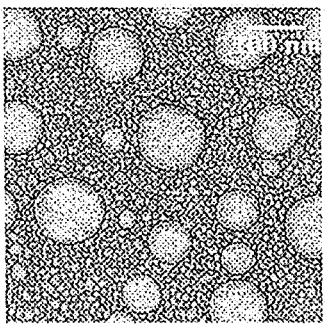
Figure 6C:
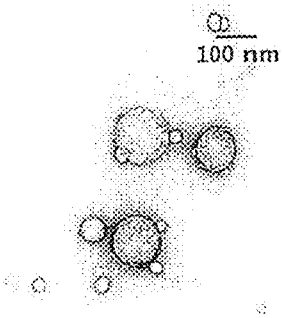

In this current study, Applicants have developed oil-in-water nanoemulsions using fish oil, which is rich in PUFAs such as omega-3 and omega-6 fatty acids and has the capability to solubilize a significant amount of lipophilic anticancer drugs. The nanoemulsion formulation was used to encapsulate DHA-SBT-1214, a second generation taxoid as a standalone therapy against prostate cancer. Applicants used a microfluidic technique to yield a uniform, milky-white emulsion formulation. All the nanoemulsions were near spherical in structure with a size range of 100-220 nm, as observed with transmission electron microscopy (TEM) (FIGS. 6A-6C). In the TEM image, both NE-Placebo and NE-DHA-SBT-1214 were taken at 60000× magnification but Abraxane was taken at 40000× magnification. The oil droplets of the nanoemulsion sample were spherical, and their size was in the range of 100-220 nm. The scale bar represents a distance of 100 nm. Particle size, polydispersity index (PDI), and zeta potential (surface charge) were determined for placebo, DHA-SBT-1214 loaded nanoemulsion formulations and ABRAXANE®. All the formulations made by microfluidic technique and filtered through 0.2-micron filter had small size (<230 nm) and narrow PDI (<0.3) except ABRAXANE® which has PDI of 0.361 and were negatively charged. TABLE 1 shows the average particle sizes, PDI and zeta potentials of all formulations used in the present study.

TABLE 1

Particle size and surface charge characterization of blank and DHA-SBT-1214 containing oil-in-water nanoemulsion formulations

| Formulations | Hydrodynamic Diameter (nm) | Polydispersity Index | Surface Charge (Mv) |
|---|---|---|---|
| Abraxane ® | 134.1 ± 6* | 0.361 | −20.2 ± 2.3 |
| Blank Nanoemulsion | 225 ± 7 | 0.11 | −27.0 ± 3.7 |
| DHA-SBT-1214 Nanoemulsion | 228 ± 7 | 0.12 | −24.9 ± 4.3 |

*Mean ± S.D.

Figure 7A:
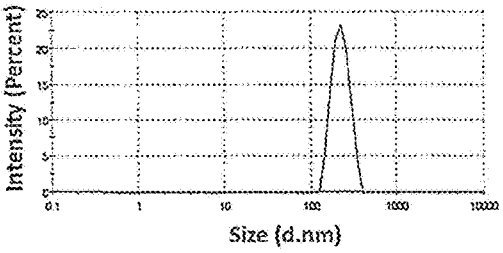
FIG. 7A is a graph of particle size determination in nm.
Figure 7B:
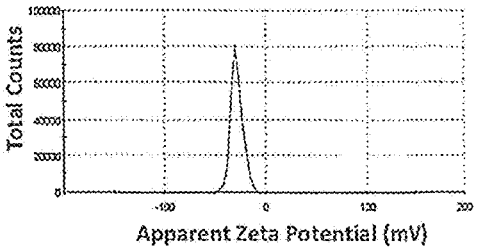
FIG. 7B is a graph of zeta potential determination in mV.

Representative graphs of size and zeta potential of DHA-SBT-1214 nanoemulsion formulations are shown in FIGS. 7B and 7C respectively. The average particle size of the blank nanoemulsion (without any drug) was 225±7 nm. The incorporation of DHA-SBT-1214 in nanoemulsions did not significantly change the hydrodynamic particle size and size and it remained at approximately 228±7 nm. ABRAXANE® showed smaller particle size compared to both nanoemulsion formulations. The average surface charge of the oil droplets in the nanoemulsions were in the range of −20.2 to −27.0 mV. Surface charge of all the formulations was not significantly different employing the maximum encapsulation of the drug inside oil droplets. An HPLC assay was used to determine the drug concentrations in the nanoemulsion formulations. DHA-SBT-1214 nanoemulsion at 20 mg/ml had the drug loading of 97%. This high drug encapsulation efficiency of nanoemulsions was attributed to the relative lipophilicity of the drugs, as these drugs retained in the oil core of the nanoemulsions. Additionally, all the formulations retained their particle size and surface charge during storage, and drug encapsulated nanoemulsion formulations were chemically stable for at least up to 6 months upon storage at 4° C. All the formulations had minimum level of endotoxin as confirmed through Limulus Amebocyte Lysate (LAL) assay during storage period.

In Vitro Evaluations of NE DHA-SBT-1214 in PPT2 CSCs

Figure 8A:
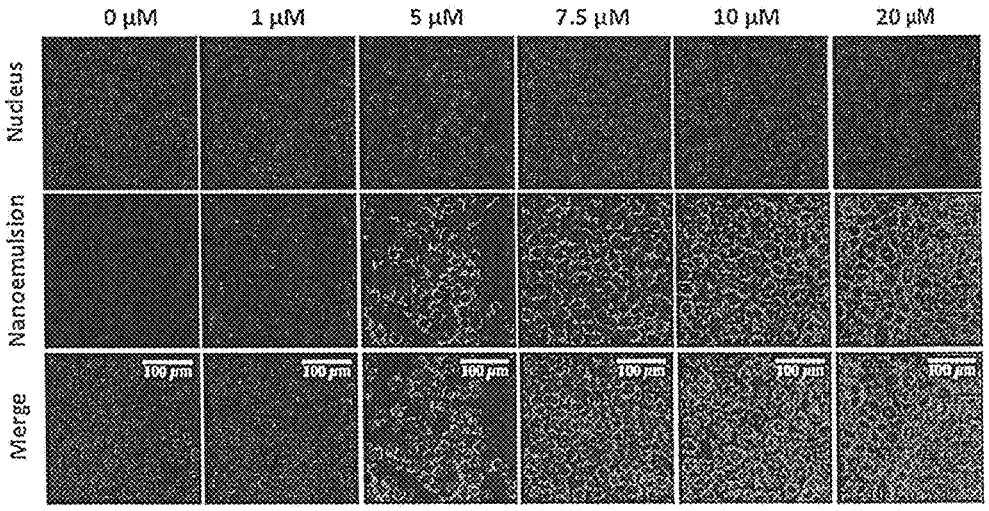
FIG. 8A is a fluorescence microscopy image of the uptake of rhodamine encapsulated nanoemulsion formulation in monolayer PPT2 cell culture, and FIG. 8B a fluorescence microscopy image of the uptake of rhodamine encapsulated nanoemulsion formulation in spheroid PPT2 cell culture.
Figure 8B:
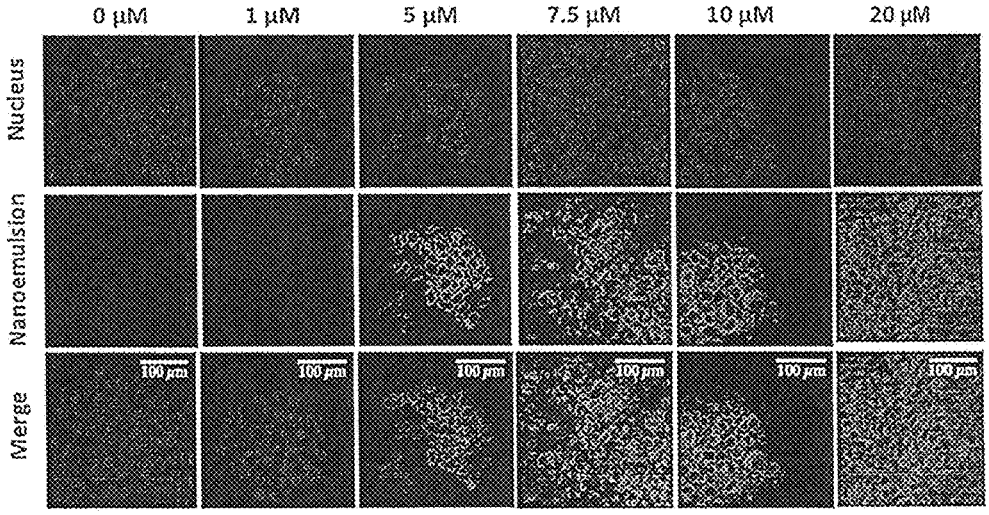

To examine whether nanoemulsions were internalized in monolayer and in spheroids of PPT2 cells, rhodamine was encapsulated into nanoemulsions and confocal microscopy studies were performed. The optimal cell and spheroid uptake of rhodamine encapsulated nanoemulsion formulation was observed after 8 hours incubation with different concentrations of the dye formulations as shown in FIGS. 8A and 8B. The fluorescence microscopy images show the blue (nucleus), red (rhodamine encapsulated nanoemulsion) and overlay images in purple color. The images were taken at 63× magnification. Scale bar is 100 μm. The images from FIGS. 8A and 8B clearly indicate that the nanoemulsions do efficiently deliver the encapsulated dye in the cells and that the increased fluorescence signal at higher the concentration of rhodamine nanoemulsion treated cells and spheroids indicates the higher intracellular uptake by PPT2 cells and spheroids. Since the internalization of nanoemulsion formulation was confirmed by cell uptake experiments, rhodamine was replaced with DHA-SBT-1214 in the nanoemulsion formulation and compared its effect on cell viability with drug solution. The cell-kill efficiency of DHA-SBT-1214 in aqueous solution and in the nanoemulsion formulations was examined in PPT2 cells monolayer using the CellTiter assay. The final concentrations of DHA-SBT-1214 selected for these studies were 1, 10, 100 and 1000 nM based on study of SBT-1214. The dose-response studies against DHA-SBT-1214 as a single agent in PPT2 cells are summarized in TABLE 2 and shown in FIG. 9A.

TABLE 2

DHA-SBT-1214 nanoemulsion formulations are more potent compared to their solution form in PPT2 prostate tumor cells

| Formulations | $IC_{50}$ (nM) | P value |
|---|---|---|
| DHA-SBT-1214 Solution | 47.9 ± 1.15* | |
| DHA-SBT-1214 Nanoemulsion | 3.73 ± 0.63 | 0.0023 |

*Mean ± S.D

The results are shown as percent viable cells remaining as a function of treatment following 48 hours of drug exposure at 37° C. When DHA-SBT-1214 was administered at 10 and 100 nM concentrations, higher cytotoxicity was observed with the nanoemulsion as compared to the aqueous solution formulation. The DHA-SBT-1214 solution $IC_{50}$ for the PPT2 cells was 48 nM, whereas the $IC_{50}$ for the same cells with DHA-SBT-1214 nanoemulsion formulation was 4 nM. This revealed that PPT2 cells needed at least ~12-fold higher concentration of DHA-SBT-1214 solution to achieve a similar $IC_{50}$ as compared to its counterpart drug nanoemulsion formulation, demonstrating the superior efficacy of nanoemulsion formulation over drug solution.

In order to confirm if DHA-SBT-1214 nanoemulsion also kill PPT2 cell spheroids, equal numbers of spheroids were treated with different concentration of DHA-SBT-1214 nanoemulsion ranging from 0.01 to 10 μM and after specific time and observed their phenotype with bright filed microscope. FIGS. 9B-9G show bright, healthy spheroids in the untreated sample which becomes dark brown with the increase in concentration displaying enhanced cell death by increasing the drug encapsulated nanoemulsion.

PPT2 Cell Line and CSC-Based In Vivo Xenograft Model

Figure 10A:
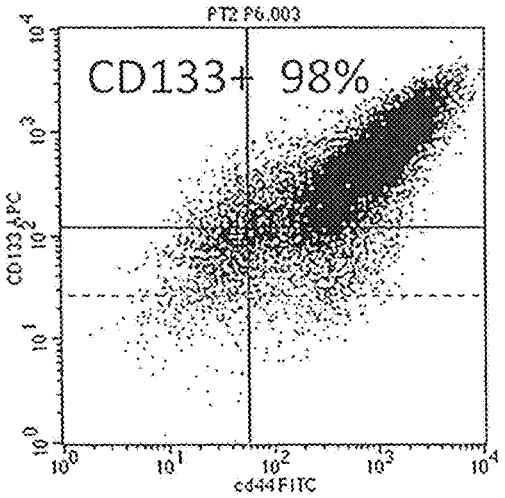
FIGS. 10A-10D are flow cytometry analysis of cell surface markers expression in parental PPT2 cell lines (CD133+ (FIG. 10A)) and CD44+ (FIG. 10B), and primary cell suspension from PPT2-induced mice tumor xenografts (CD133+ (FIG. 10C)) and CD44+ (FIG. 10D)
Figure 10B:
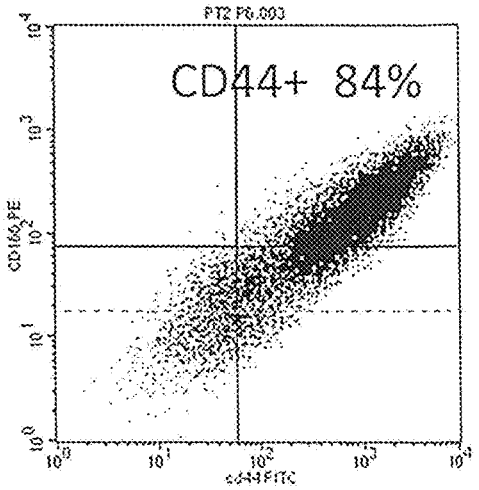
Figure 10C:
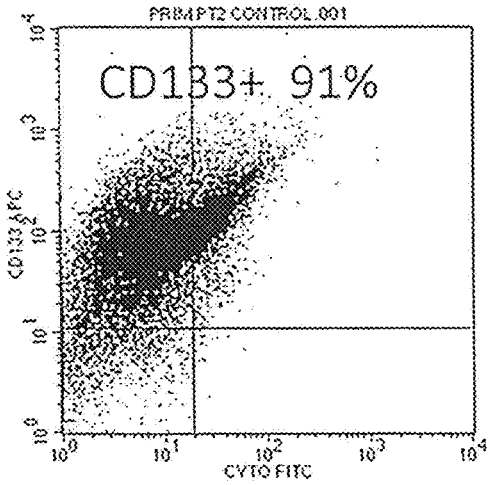
Figure 10D:
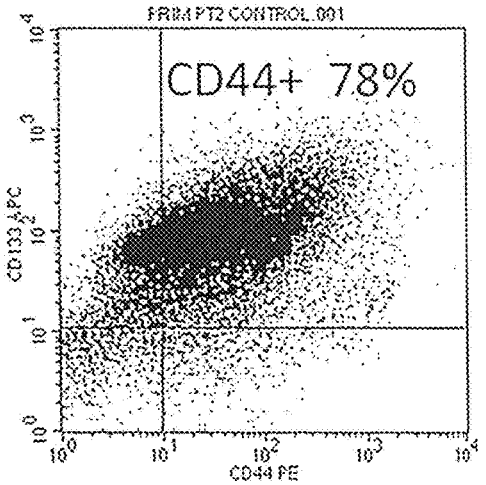

The vast majority of the recently established PPT2 cells remains undifferentiated (only 3-5% express pan-keratin, a marker of differentiated cells), possess many stem cell characteristics, including high levels of expression of many common cell surface markers, such as CD133, CD44, CD44v6, CD166, CD49f and EpCAM. In addition, the PPT2 cells express several markers of pluripotency, including c-Myc, Oct-4 and Sox-2 amongst others. The vast majority of the $CD133^+$ PPT2 cells expressed high cytoplasmic levels of vimentin and nestin, characteristic of neural and embryonic stem cells. About 10% of the total population of the PPT2 cells with the highest expressions of CD133 and CD44 co-expressed the highest levels of the CXCR4, the chemokine receptor associated with metastatic activity in several cancer types. Importantly, PPT2 cells are negative for pro-apoptotic/tumor suppressor proteins, p53 and p21, and extremely resistant to standard anti-cancer drugs. The PPT2 cells stably possess very high clonogenic (holoclones), sphere-forming and tumorigenic capacities. In addition, these cells are extremely resistant to drug treatment. All of the above represents solid arguments for the utilization of the PPT2 cell line for evaluation of CSC-targeted efficacy of anticancer drug candidates. Although even several thousand of PPT2 cells uniformly induced tumors in NOD/SCID mice, Applicants have determined that subcutaneous transplantation of relatively high number of cells (up to 1 million cells per mouse) induces tumor xenografts with unusually high percent of stem-like cells. Thus, if transplanted cells contained up to 98% of $CD133^+$ cells and 84% of $CD44^+$ cells (FIGS. 10A and 10B), the primary cell suspension prepared from mice tumor xenografts contained up to 91% of $CD133^+$ cells and 78% of $CD44^+$ cells (FIGS. 10C and 10D). All these features show that the PPT2 in vivo and in vitro models are suitable for testing the CSC-targeted activities of the NE-DHA-SBT-1214.

Growth Inhibition of PPT2 Tumors in NOD/SCID Mice

Figure 11H:
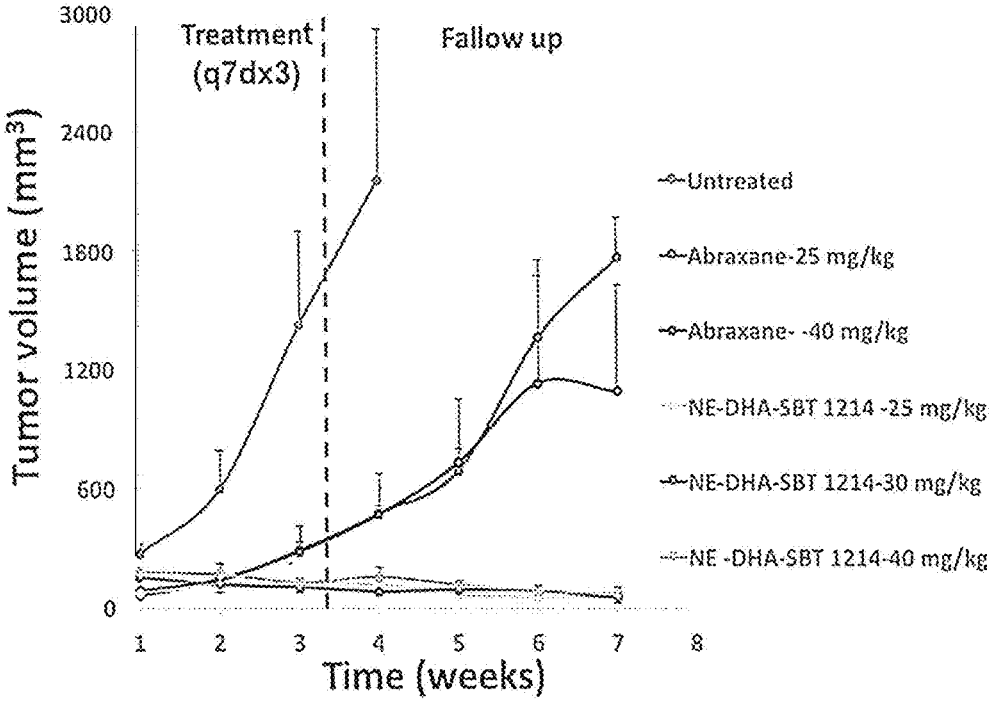
FIG. 11H is a graph summarizing all treatment modalities.
Figure 12A:
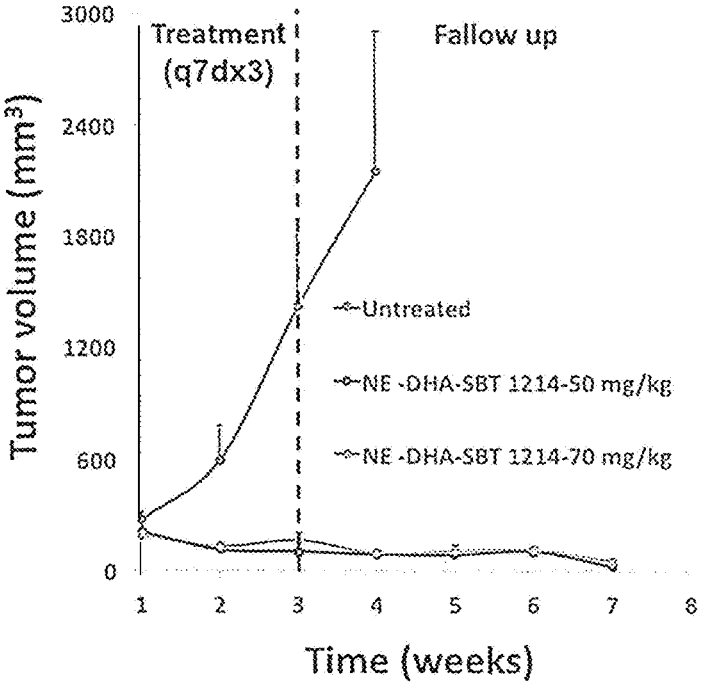
FIG. 12A is a graph of tumor volume change over time employing in vivo efficacy of the NE-DHA-SBT against PPT2 induced mice tumor xenografts.
Figure 12B:
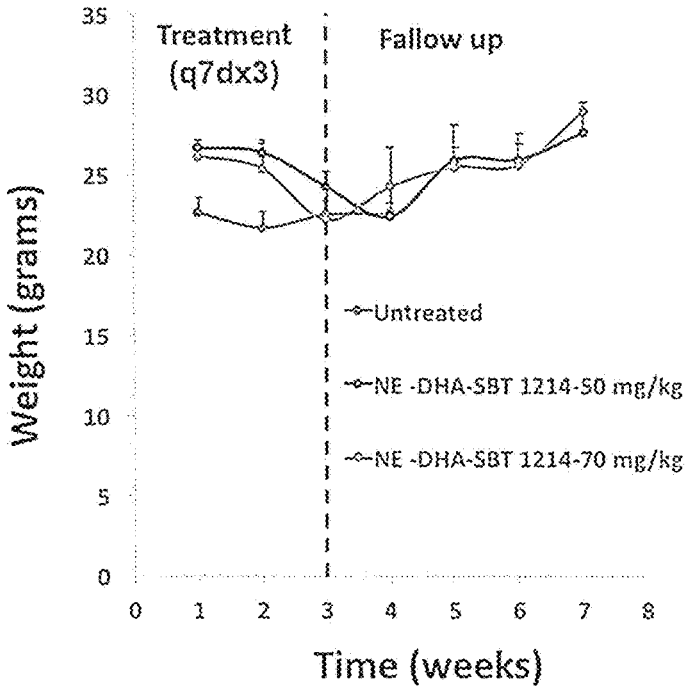
FIG. 12B is a graph of body weight alterations induced by treatment with different concentrations of NE-DHA-SBT.

All animal procedures were carried out under the guidelines and approval of the institutional animal care and use committee (IACUC). After transplantation of the PPT2 cells, NOD/SCID mice were divided into particular number of groups for weekly treatment by intravenous injections of NE-DHA-SBT-1214 (25, 30, 40, 50 and 70 mg/kg), ABRAXANE® [25 and 40 mg/kg; ABRAXANE® is Cremophor® EL-free nanoparticle albumin-bound paclitaxel), and vehicle (untreated control). Each dose group contained four mice (n=4; group treated with 25 mg/kg of NE-DHA-SBT-1214 had n=6). Treatment was started one week after transplantation of the tumor cells, when tumor xenografts became palpable (tumors usually reached 50-150 $mm^3$). Tumor development was monitored weekly. After 3 sets of weekly injections, tumor growth was monitored for additional 4 weeks, and all the measurements and morphology are presented in FIGS. 11A-11F. It was found that in contrast to ABRAXANE® (FIGS. 11B, 11C), even relatively low concentrations of NE-DHA-SBT-1214 induced dramatic suppression of tumor growth (FIGS. 11D, 11E, 11F) compared to untreated tumor xenografts (FIG. 11A), and dose dependent reduction of tumor volume compared to the initial tumor size (FIG. 11H). Thus, all tested concentrations of the NE-DHA-SBT-1214 induced tumor shrinkage (with the exception of 1 of 6 mice treated with lowest dose of NE-DHA-SBT-1214, 25 mg/kg). All the residual post-treatment tumors were virtually transparent, without a visible vascularization. Maximal tumor regression was observed by the $4^{th}$ week of follow-up. In particular, 25 mg/kg induced in average 45% shrinkage, 30 mg/kg—62%, 40 mg/kg—74% and 50 mg/kg—88% (FIG. 12A) reduction of tumor volume. Of note, higher dose of NE-DHA-SBT-1214 (70 mg/kg) (FIG. 12A) did not augment tumor reduction. In contrast to NE-DHA-SBT-1214, the optimal dose of ABRAXANE® (25 mg/kg) and even 40 mg/kg caused only insignificant suppression of the PPT2-induced tumor growth for about 4 weeks followed by continued growth at the rate similar to untreated mice xenografts (FIG. 11H). Although the tumor growth inhibition and tumor shrinkage in all mice treated with different concentrations of NE-DHA-SBT-1214 was dramatic, all mice lost up to 17% of body weight by third week of treatment (FIG. 11G and FIG. 12B). However, from the second week of follow-up, all mice started to gain weight. No significant body weight changes were induced by treatment with Abraxane. Four weeks after the last treatment, the residual tumors from different experimental groups were harvested and subjected to histopathological, genomic and functional analyses. Untreated control tumors were removed upon reaching approximately 2 cm in largest diameter in accordance with the IRB requirements.

Tissue Histopathological Analysis

Figure 13A:
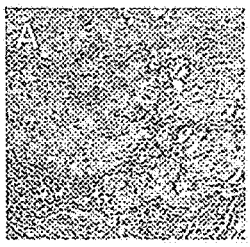
FIGS. 13A-13L are photographs showing histopathological evaluation of the PPT2-induced tumor and different organ tissues collected from control and NE-DHA-SBT treated mice (hematoxylin & eosin staining), FIG. 13A—control untreated tumor shows poorly differentiated adenocarcinoma.
Figure 13B:
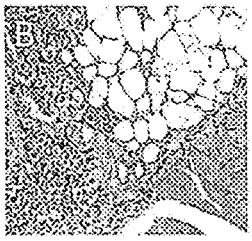
Figure 13C:
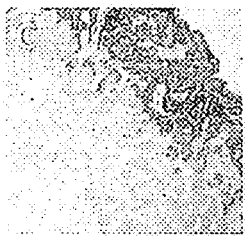
Figure 13D:
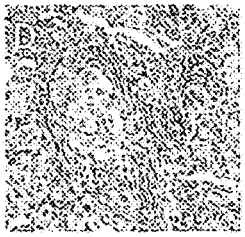
Figure 13E:
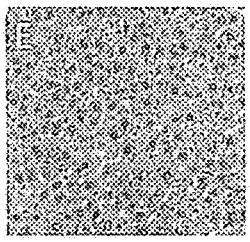
Figure 13F:
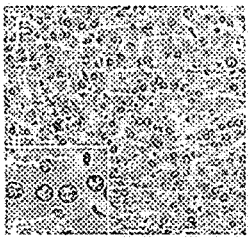
Figure 13G:
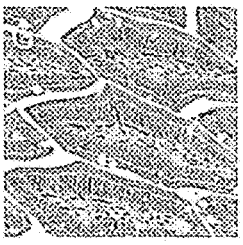
Figure 13H:
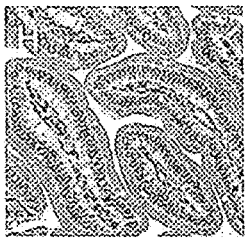
Figure 13I:
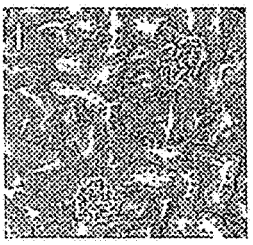
Figure 13J:
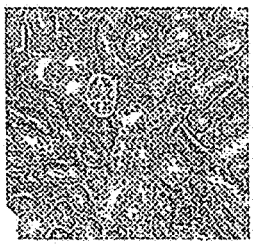
Figure 13K:
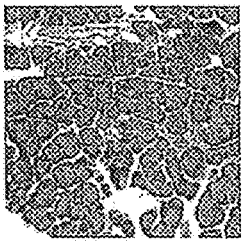
Figure 13L:
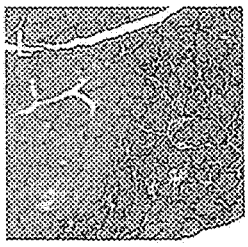
Figures 18A, 18B, 18C, 18D:
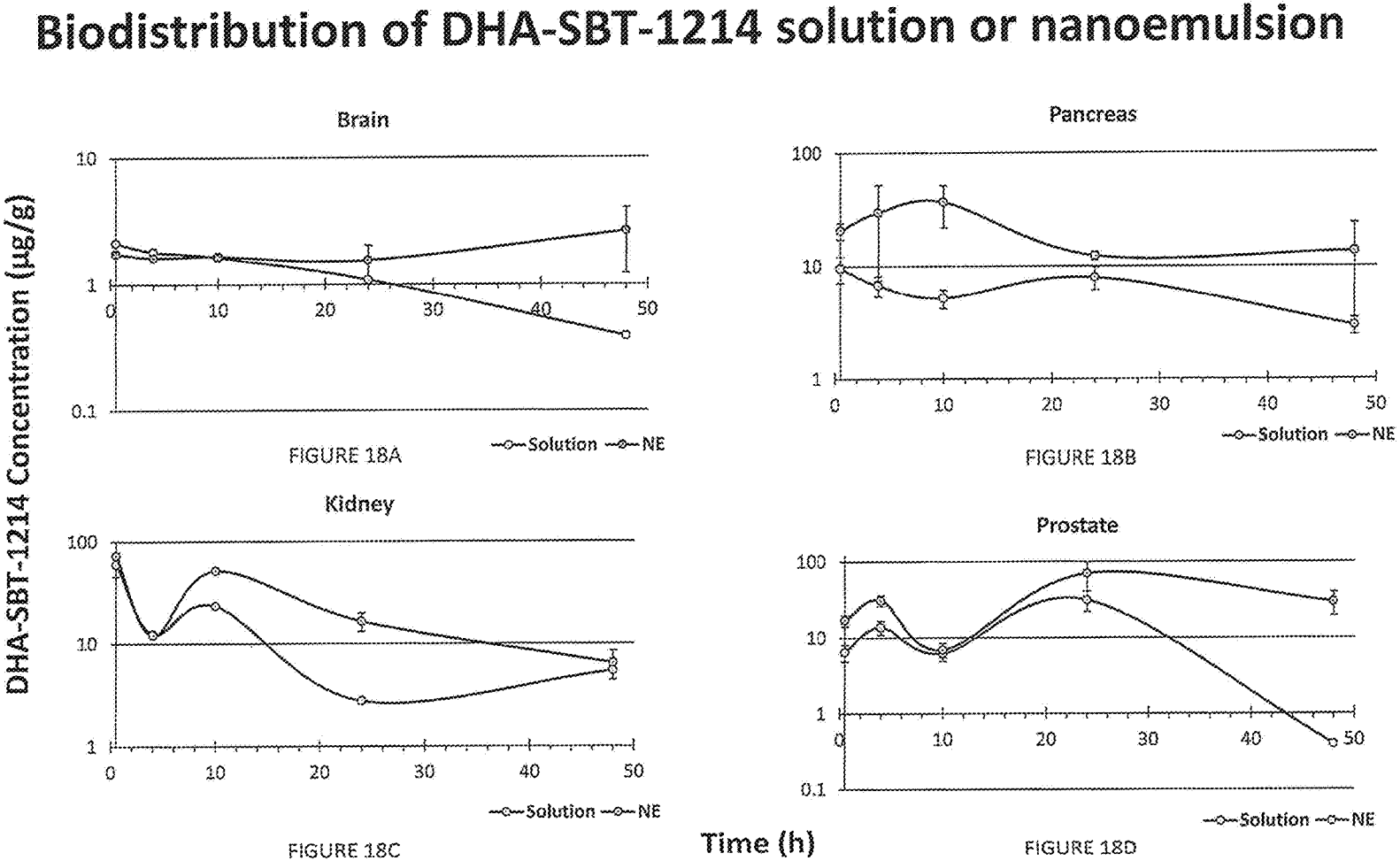
FIGS. 18A-18K are graphs of the biodistribution of DHA-SBT-1214 solutions and nanoemulsions in the brain (FIG. 18A), pancreas (FIG. 18B), kidney (FIG. 18C), prostate (FIG. 18D), colon (FIG. 18E), heart (FIG. 18F), lung (FIG. 18G), liver (FIG. 18H), spleen (FIG. 18I), plasma (FIG. 18J), and tumor (FIG. 18K)
Figures 18E, 18F, 18G, 18H:
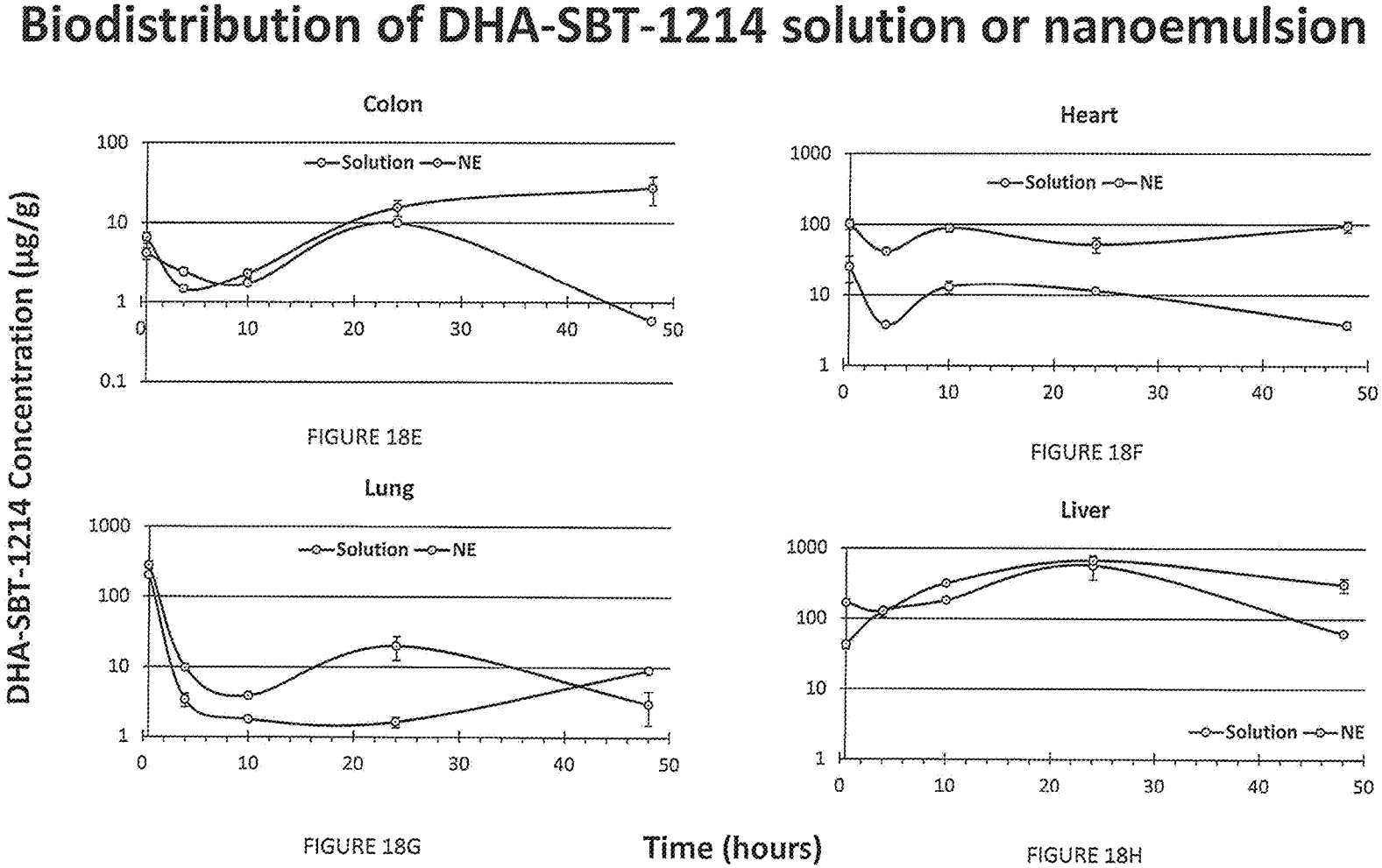
Figure 18J:
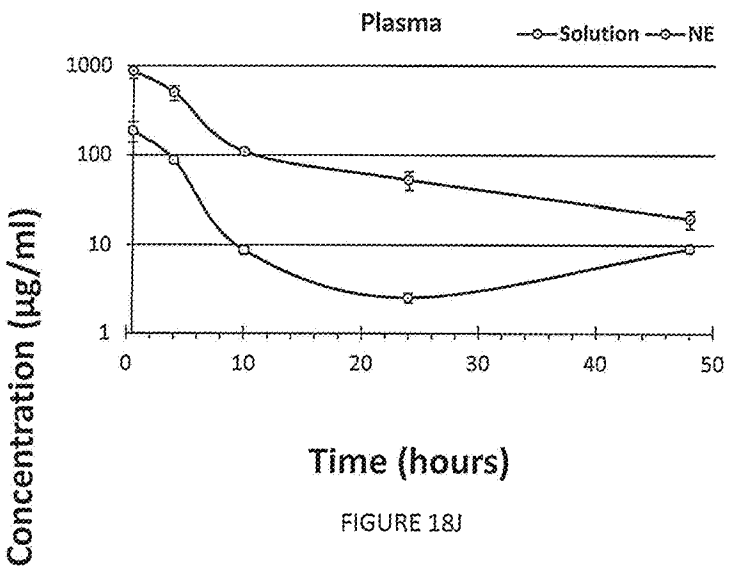
Figure 18I:
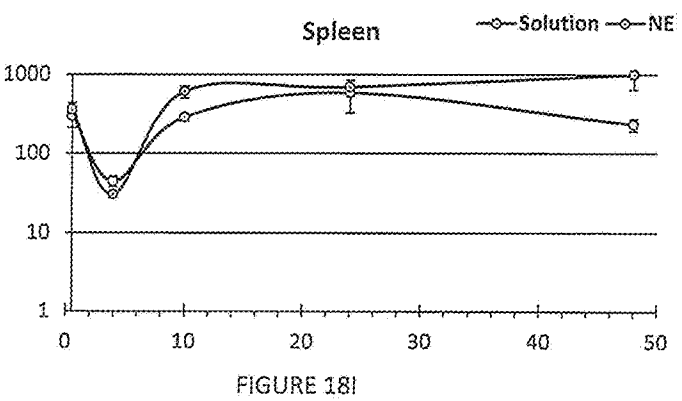
Figure 18K:
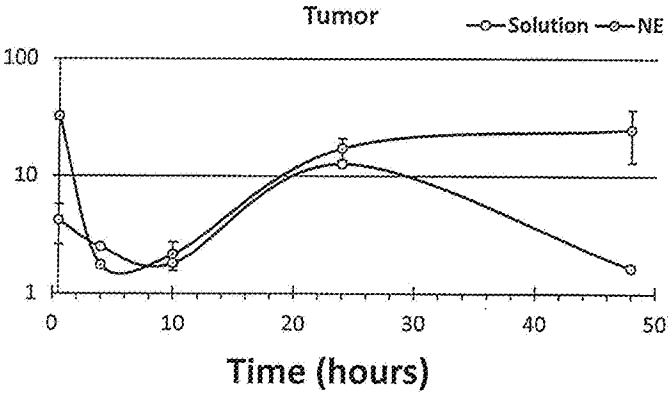

The hematoxylin and eosin stained tumor xenografts tissue sections were analyzed, as well as tissue sections of several major organs, including liver, kidney, intestine and pancreas, from the untreated and NE-DHA-SBT-1214 treated NOD/SCID mice. Control untreated tumor tissue sections show classic histologic features of human poorly differentiated adenocarcinoma with a great degree of nuclear atypia (FIG. 13A). The NE-DHA-SBT-1214 (30 mg/kg) treated tumor tissues showed significant cellular abnormalities, profound hyalurization, vacuolization and extensive necrosis (FIGS. 13B-13D). Among histologically evaluated major organs, such as liver (FIG. 13E), kidney (FIG. 13I), intestine (FIG. 13G), pancreas (FIG. 13K), only liver tissue from NE-DHA-SBT-1214 treated mice (40 mg/kg) showed reactive nuclear changes of hepatocytes, suggestive of some injury (FIG. 13F). Other organs did not show any diagnostic abnormalities (FIGS. 13H, 13J and 13L).

Post-Treatment Alterations in Clonogenic and Sphere-Forming Capacities of Tumor Cells To test whether or not treatment with NE-DHA-SBT-1214 affects the clonogenic potential of the CSC-enriched mice tumor xenograft cells i. e. their ability to induce floating spheroids or adherent round colonies (holoclones), total cell suspensions from the control, and NE-DHA-SBT-1214-treated residual tumors (ex vivo cell culture) were seeded on type 1 collagen-coated dishes and ULA plates. Untreated (vehicle-treated) PPT2-induced tumor xenografts were densely vascularized (FIGS. 14A and 14B) and the NE-DHA-SBT-1214 treated residual tumors were very small, transparent, lacked visible capillaries (FIGS. 15A and 15B) and did not produce adherent holoclones, with only sporadic appearance of a single spheroids in 3D cultures. These Primary tumor cells underwent profound cell death in the next several days in culture as shown by percent viable cell data of untreated spheroids (FIG. 16) and NE-DHA-SBT-1214 treated spheroids (FIG. 17), grown from primary tumor cell suspensions. Percent of survived cells is shown on lower left quadrants and dead cells are in lower right quadrant.

Discussion

It is largely documented that the tumor-initiating cells, or CSCs, are not only highly resistant to conventional therapeutic strategies, but may actually promote cancer progression due to the drug induced compensatory increase in their self-renewal. This highlights the need for effective therapeutic interventions targeted the CSCs. The studies were performed on patient-derived, CSC-enriched PPT2 cell line, the stemness features of which were previously described and constantly maintained in the laboratory. The observed over-activation of several developmental cascades in PPT2 cells, such as Hedgehog, EGFR, Wnt/β-catenin and Notch, was linked with prostate stem cell regulation and the progression of prostate cancer to androgen-independence and metastasis. The involvement of SOX2 and OCT3/4 in prostate metastasis was demonstrated by targeted knockdown of these genes, which markedly suppressed the invasion of prostate cancer cells in vitro. Both vimentin and nestin were associated with the transition from androgen-dependent to castration-resistant metastatic prostate cancer. Therefore, it would be beneficial to develop drugs targeting CSCs from the most aggressive tumor types or cell lines, because such drugs can potentially have a larger spectrum of mechanisms of action, and therefore, broader anti-cancer implications. Increasing evidence indicates that effective anticancer drugs should target cancer-specific tumor-initiating cells, which are functionally and morphologically different from their bulk tumor counterparts. All of the above shows that the PPT2 cells represent a unique pre-clinical model for CSC-targeted drug development and basic functional studies of prostate cancer development.

It was recently shown that drugs targeting major stem cell signaling pathways, such as Hedgehog and Notch, induce serious side effects on normal stem cells. The inhibition of the drug efflux pumps in attempt to modulate drug resistance of CSCs did not provide any significant clinical benefit. Accumulating clinical and preclinical evidence indicated that the benefits of antiangiogenic agents to the long-term survival of cancer patients was negligible. Microtubule stabilizers such as paclitaxel (Taxol) and docetaxel can be initially effective in treating patients with androgen-independent prostate cancer, but the cancer almost invariably recurs in a more aggressive form. Paclitaxel, is still front-line treatment for many solid tumor indications including breast, ovarian, and non-small cell lung (NSCLC) cancers as well as Kaposi's sarcoma. Paclitaxel exerts its potent cytotoxicity through binding to β-tubulin, hyperstabilizing microtubules and impairing the dynamic instability of the microtubule framework. This causes cell cycle arrest and initiation of apoptosis at the G2/M stage. In order to manage its poor aqueous solubility, numerous formulations as well as prodrugs of paclitaxel have been developed, including liposome, cyclodextrin and HSA-bound nanoparticle ("ABRAXANE®") formulations. Paclitaxel is not effective against prostate and colon cancer due to the over expression of P-glycoprotein (Pgp), an effective ATP-binding cassette (ABC) transporter, which effluxes paclitaxel. Accordingly, paclitaxel does not show any appreciable efficacy even against human colon cancer xenografts in mice.

In order to overcome efflux issue, Paclitaxel was conjugated with polyunsaturated fatty acids (PUFAs), docosahexaenoic acid (DHA) due to its cancer specific activity, protective effect on healthy cells and enhanced tumor-specific accumulation of the drug conjugates through gp60-mediated transcytosis into the tumor interstitium. This is due to higher affinity of DHA conjugated drug to human serum albumin (HAS) which is the primary carrier for PUFAs in the bloodstream. DHA-paclitaxel (TXP) is voraciously taken up by tumor cells, internalized, and slowly hydrolyzed by esterases in the cancer cell. DHA paclitaxel was found to be a relatively weak substrate for Pgp as compared to paclitaxel, as mentioned above. However, if the cancer cells are overexpressing Pgp and/or other ABC transporters, free paclitaxel molecules, even when released slowly, will be caught by the efflux pump(s) and eliminated from the cancer cells. In contrast to paclitaxel, a new generation taxoid, SBT-1214, shows excellent activity (2-3 orders of magnitude more potent than paclitaxel) against drug resistant cancer cells, expressing multidrug resistant (MDR) phenotypes. Previously Applicants have shown that this new-generation taxoid SBT-1214 induced long-term (167 days) regression and tumor growth delay of drug resistant colon tumor xenografts. Later, it was found that this drug molecule induced significant down-regulation of multiple stemness-related genes, including several key transcription factors involved in the regulation of stem cells, cancer development and progression. Of note, docetaxel (standard first-line therapy in metastatic castration-resistant prostate cancer) can promote drug resistance and de-differentiation (epithelial to mesenchymal transition) of prostate cancer cells via TGF-beta mechanism. In order to further improve blood circulation and ultimately therapy, DHA was conjugated to SBT-1214 in the current study.

To further improve delivery of this hydrophobic drug delivery, DHA-SBT-1214 was encapsulated in nanoemulsions which are thermodynamically stabilized dispersions of oil in water, where the oil droplet size is reduced to nanometer length scale (≈200) by applying high shear stress using high energy ultrasonication or microfluidizing instruments. When lipophilic drugs are incorporated into the nanoemulsions, the pharmacokinetic and biodistribution pattern of the compounds upon systemic administration will be dictated by the properties of the nanoemulsions formulations rather the physicochemical characteristics of the drug molecules. For example, the PEG-modification can enhance the longevity of the nanoemulsions in the blood circulation. This in turn increases the residence time of the drug molecules in the blood and also allows enhanced accumulation at the tumor site through the EPR effect. In this study, Applicants have developed an optimized oil-in-water nanoemulsion formulation using fish oil, which has a high concentration of PUFA. In general, all the nanoemulsions showed oil droplet size below 250 nm with narrow size distribution. TEM image also confirms that the oil droplets were spherical and uniformly distributed. PEG surface modification of nanoemulsions using DSPE-PEG2000 did not affect the particle size and size distribution. The surface charge values of the nanoemulsions were observed in the range of −23.37 to −34.53 mV. The surface charge on the nanoemulsion oil droplets is representative of the ionization of the components forming the interfacial layer. In case of PEG-modified nanoemulsions, the interfacial layer was formed as a result of egg lecithin and PEG-modified phospholipid (DSPE-PEG2000). These formulations were used to deliver DHA-SBT-1214 against PPT2 cells and spheroids. The qualitative cellular uptake analysis demonstrated that the nanoemulsion formulations were efficiently internalized in PPT2 cells and spheroids. This suggests that the nanoemulsions do efficiently deliver the payload to the subcellular sites in the cell. It was determined that a nanoemulsion of the relatively low concentrations of DHA-SBT-1214 (0.1-1 μM) induced up to 90% death of the highly tumorigenic and highly drug resistant prostate CD133+ cells maintained under stemness-promoting culture conditions and was more potent than its drug solution. In this study, it was found that DHA-SBT-1214 suppresses PPT2 tumors when delivered in nanoemulsion formulations. In addition to these observations, flow cytometry analysis also revealed that implanted tumor cells retained their stemness inside the subcutaneous tumors. Therapy with DHA-SBT-1214 delivered in nanoemulsions indeed showed higher therapeutic efficacy in PPT2 cells and tumors. No significant body weight loss was observed in any of the treatment groups analyzed. Tissue histology did not show any abnormal findings in liver, heart or kidney in any of the treatment groups. These tests show that DHA-SBT-1214, when administered as nanoemulsion is well tolerated in mice. In conclusion, our data demonstrate that nanoemulsion of the DHA-SBT-1214 conjugate induces superior regression and tumor growth inhibition and has high potential as a novel CSC-targeted anti-cancer drug candidate.

Conclusions

In the current study, a polyunsaturated fatty acid based nanoemulsion system effectively encapsulated the hydrophobic drug, DHA-SBT-1214 and demonstrated therapeutic efficacy both in vivo and in vitro models. The formulation was also well tolerated as tested in mice. Particle size and zeta potential data demonstrated the formation of physically stable nanoemulsions. When administered in the nanoemulsion formulations, DHA-SBT-1214 was delivered inside the PPT2 cells and resulted in significant enhancement in in vitro cytotoxicity. In conclusion, the data indicate that nanoemulsion formulation of DHA-SBT-1214 has enhanced the anti-cancer efficacy compared to its solution. Therefore, a hydrophobic drug, which exert pleiotropic CSC-targeted activities against primary patient-derived, spontaneously immortalized, low passage, highly tumorigenic and clonogenic prostate cancer cells with CD133+/high/CD44+/high phenotype is clinically relevant and has high potential as an anti-cancer drug combination.

A delivery system that can be easily prepared, effectively and efficiently incorporate hydrophobic molecules, be clinically safe and improve the pharmacology of DHA-SBT-1214 is desirable. The results show that a nanoemulsion formulation of the novel taxoid DHA-SBT-1214 can provide a new therapy in difficult to treat cancers. Nanoemulsions are promising novel formulations that can enhance the therapeutic efficacy of hydrophobic drugs such as DHA-SBT-1214. In addition, one can use these nanoemulsions as the formulation of choice for screening and evaluation of experimental drug candidates that have poor water solubility. In such cases, nanoemulsions can be easily formulated thus avoiding other time consuming and costly formulation studies. Nanodelivery systems are promising vehicles in drug delivery because they improve solubility of hydrophobic drugs, such as PX, and generally have low toxicity as well. ABRAXANE®, a PX albumin-bound nanoparticle formulation with the particle size of ~130 nm, was approved by the FDA in 2005 for the treatment of metastatic breast cancer. This formulation had demonstrated some advantages in terms of reduced toxicity compared to Taxol. In addition, the total dose can be administered within 30 min without pretreatment. Accordingly, there is every indication that NE-DHA-SBT-1214 is a powerful tumor-targeting chemotherapeutic agent, overcoming the weaknesses of paclitaxel, docetaxel and TAXOPREXIN® and substantially improve the quality of life of cancer patients. There is also a growing body of evidence that taxoids have immunological effects that could be harnessed in combination with immune-oncology agents such as checkpoint inhibitors. Taxane treatment has been shown to stimulate tumor-associated macrophage cytotoxicity, induce the activation of dendritic cells, natural killer cells, tumor specific cytotoxic T-cells as well as downregulate regulatory T cells ("$T_{regs}$"). Therefore, a nanoemulsion formulation of a novel second-generation taxoid that is not a substrate for the PgP transporter, is effective against MDR tumors and cancer stem cells ("CSC's"), has an improved safety and drug delivery profile and passively targets the tumor represents a potential solution to a clear unmet medical need.

Example 5

Pharmacokinetic Analysis and Biodistribution of DHA-SBT-1214 Solution and its Nanoemulsion in PPT2 Subcutaneous Tumor Bearing Mice.

Materials

Male CD-1® mice (4-6 weeks old) were purchased from Charles River Laboratories (Cambridge, Mass.). Human primary prostate cancer cells (PPT2) were subcutaneously transplanted in the right flank of these mice to form tumors. All the animal procedures were approved by the Northeastern University's Institutional Animal Care and Use Committee. The solvents were purchased from Fisher Scientific (Fair Lawn, N.J.).

High Performance Liquid Chromatography (HPLC) Analysis

The Waters LC (model 2487, Waters Corporation, Milford), comprising of two pumps, an autosampler, and a UV-detector, was used for the analysis. The LC system was interfaced with Empower software for instrument control, data acquisition, and processing. The mobile phase, consisting of (A) 0.1% TFA in water, and (B) 0.1% TFA in acetonitrile, was pumped through the Grace Vydac 218TP54 column (C18, particle size 5 μm, 4.6 mm×250 mm) at a flow rate of 1 mL/min. The gradient was 60% B to 95% B in 15 min and drug elution was monitored at a wavelength of 230 nm. 80 μL aliquot of was injected into the HPLC.

Plasma Pharmacokinetic Analysis of DHA-SBT-1214 Solution and Nanoemulsion Formulation DHA-SBT-1214 was dosed intravenously as solution or nanoemulsion formulation to mice, via tail vein injection at 120 mg/kg. Blood was collected in EDTA-treated tubes at various time intervals: 0.5, 4, 10, 24 and 48 hours post dosing and kept on ice. The samples were centrifuged at 10,000 rpm for 20 minutes at 4° C. to separate plasma. The plasma was stored at −20° C. or used immediately for analyses. 100 μl of plasma was constituted with 300 μl of acetonitrile, and following vortexing, centrifuged at 10,000 rpm for 10 min to extract and separate DHA-SBT-1214. HPLC was performed on the supernatant and the elute analyzed by HPLC.

Biodistribution of DHA-SBT-1214 Solution and Nanoemulsion Formulation in Different Tissues DHA-SBT-1214 was dosed intravenously as solution or nanoemulsion formulation to mice, via tail vein injection at 120 mg/kg. Following intravenous dosing of DHA-SBT-1214, the mice were anesthetized and at pre-determined time points of 0.5, 4, 10, 24 and 48 hours, the blood was completely withdrawn by cardiac puncture. Animals were perfused with PBS and then sacrificed via cervical dislocation and various tissues including heart, prostate, pancreas, brain, colon, lungs, spleen, kidneys, liver and tumor tissues were harvested, weighed, snap frozen in liquid nitrogen and stored at −80° C. The frozen tissues were suspended in equivalent weight of normal saline solution and homogenized using a tissue homogenizer at 5000 rpm for 2 minutes. 4-fold excess mixture of Ethyl acetate:methanol: acetonitrile (50:25:25) was added to homogenized tissue and following vortexing, the sample was centrifuged at 10,000 rpm for 10 min at 4° C. to extract and separate DHA-SBT-1214. Supernatant was evaporated with nitrogen gas and sample reconstituted in 400 μl of acetonitrile. HPLC was performed on the reconstituted sample and the eluent analyzed by HPLC.

Pharmacokinetic Data Analysis

DHA-SBT-1214 pharmacokinetic parameters were determined using non-compartmental analysis with Phoenix® WinNonlin® v. 1.3 software. Area under the plasma concentration-time curve from zero to infinity (AUC0-∞) was calculated using the log-linear trapezoidal method. PK parameters including volume of distribution at steady state (Vss), clearance (Cl), lambda z (λz) which is the rate constant associated with terminal elimination phase, corresponding half-life (t½), and mean residence time (MRT), were estimated.

Results

PPT2 cells were implanted in 5 weeks old male NOD-.SCID/NCr mice. When tumor volume reached to an average of 100 $mm^3$, mice were randomized into two groups. One group was treated with DHA-SBT-1214 solution and the other group of mice with a nanoemulsion of the same drug by intravenous dosing at 120 mg/kg of mice for different time points (0.5, 4, 10, 24 and 48 hours). There were two mice per timepoint for each treatment. Each organ was divided into two to have four replicates for each timepoint. Tumor volumes were 100 to 150 $mm^3$. After each time point is over, the animal was scarified and all major organs and tumor were harvested and blood was collected. DHA-SBT-1214 drug was extracted with acetonitrile from all organs and plasma and quantified through HPLC method. FIGS. 18A-18K, show the biodistribution of drug from both solution and nanoemulsion in different organs. In almost all the organs, drug from the nanoemulsion is retained for a longer time compared to its solution form. Higher retention of drug in different organs even after 48 hours shows that nanoemulsions keeps the drug in blood circulation for a longer time and hence it can provide more exposure of tumor vascular to the drug in order to have better therapeutic efficiency compared to currently used drug solutions.

Example 6

Stability of DHA-SBT-1214 Nanoemulsion Formulation

Figure 19A:
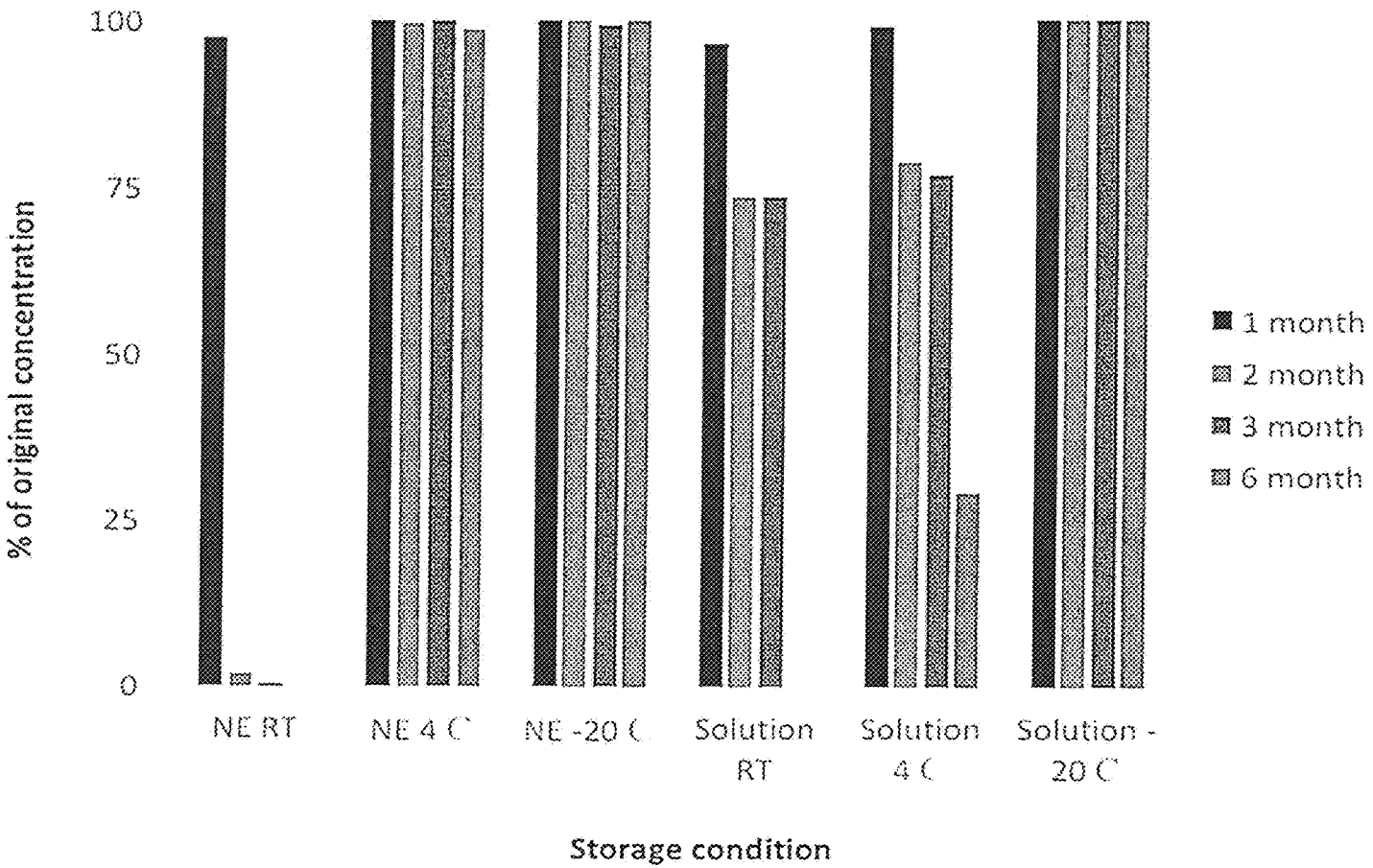
FIGS. 19A-19D are graphs of stability properties over time and temperatures for DHA-SBT-1214 drug solution and nanoemulsions.
Figure 19B:
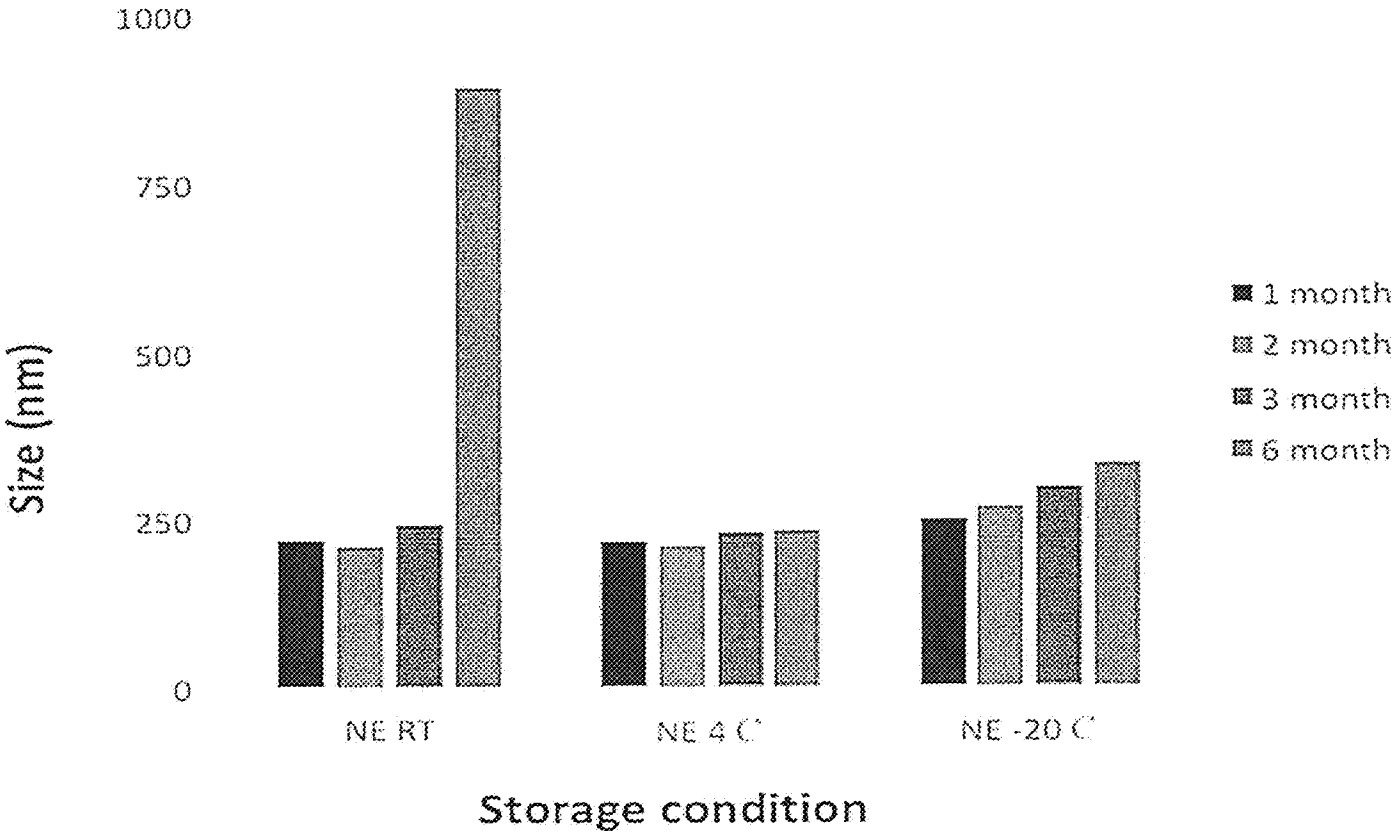
Figure 19C:
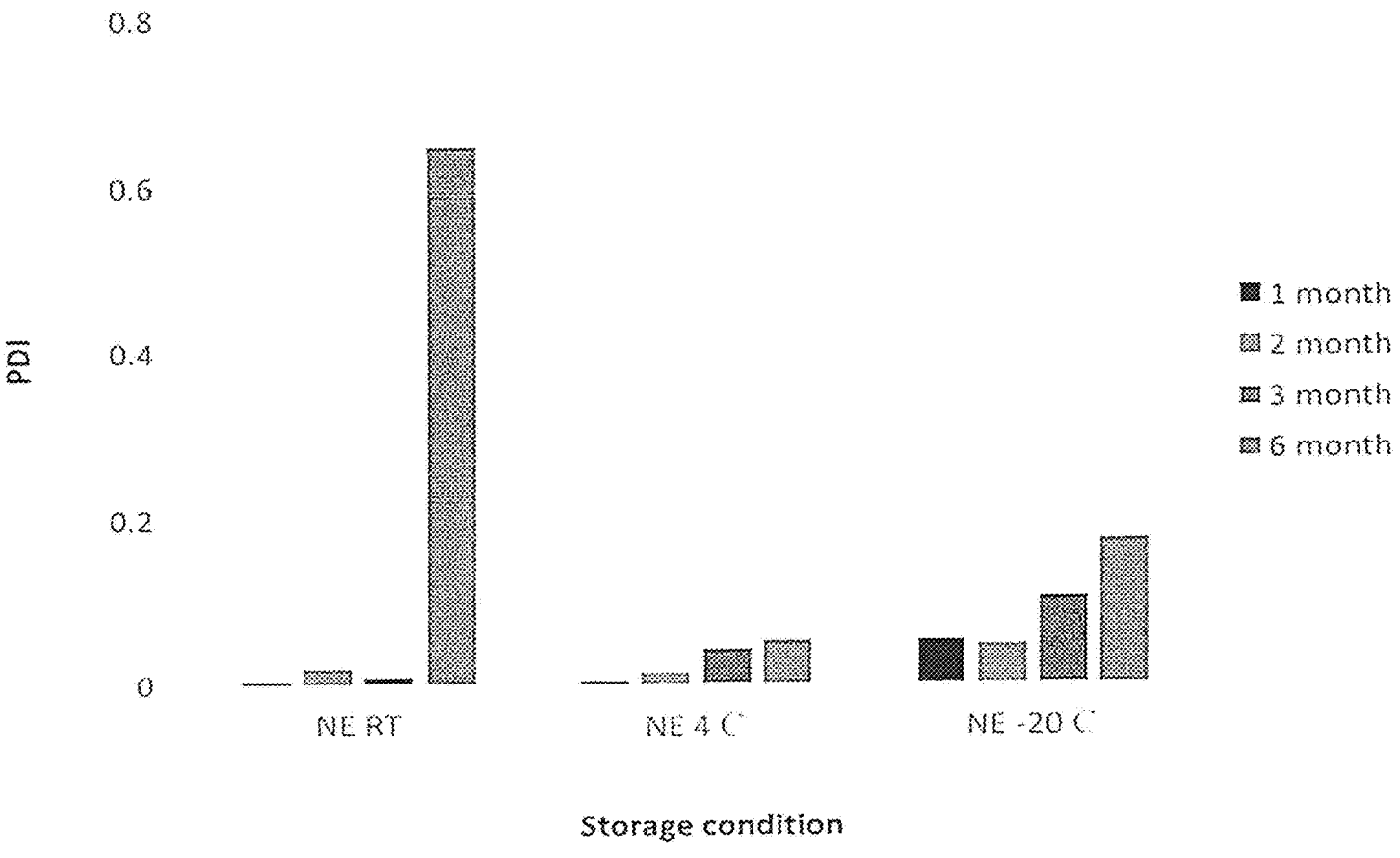
Figure 19D:
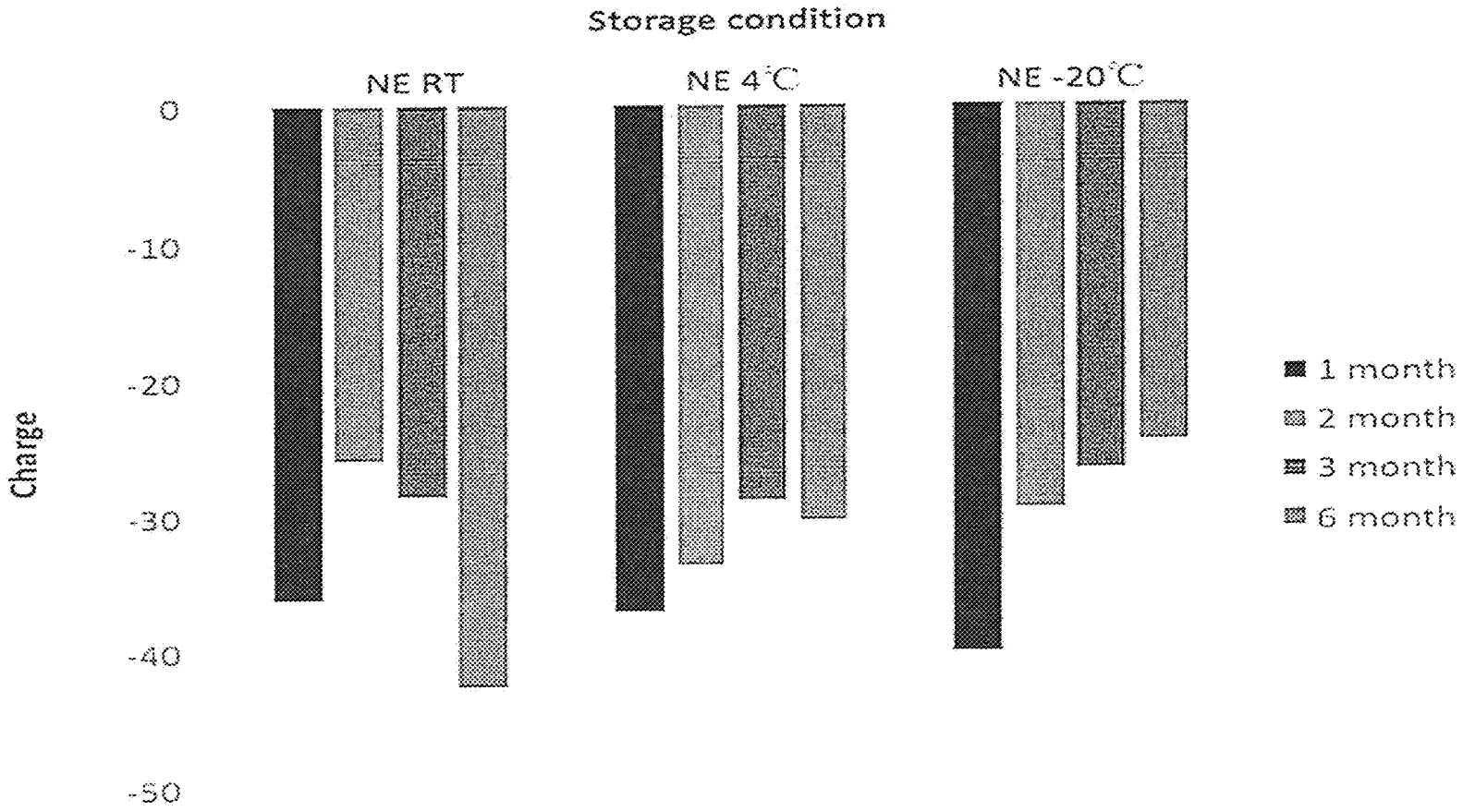
Figure 20A:
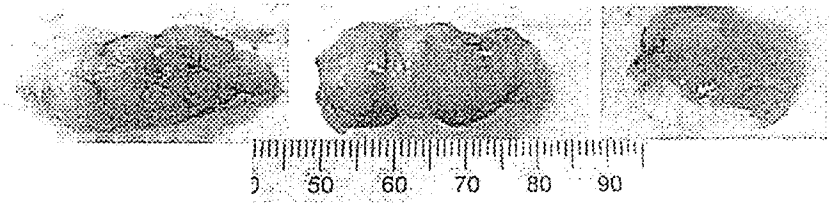
FIGS. 20A-20E are photographs of tumors with different treatment groups: control (FIG. 20A), NE-DHA-SBT 30 mg/kg (FIG. 20B), NE-DHA-SBT 40 mg/kg (FIG. 20C), NE-DHA-SBT 50 mg/kg (FIG. 20D), and NE-DHA-SBT 70 mg/kg (FIG. 20E)
Figure 20B:
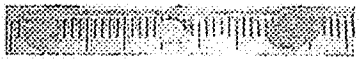
Figure 20C:
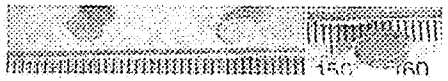
Figure 20D:
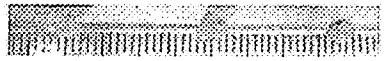
Figure 20E:
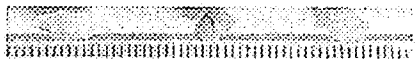

Nanoemulsions were studied for stability with respect to its uniformity (appearance), particle size and surface charge up to 6 months after storage at different temperatures. DHA-SBT-1214 solution and nanoemulsion from three different batches were incubated at different storage conditions, i.e. room temperature, 4° C., and −20° C. for up to 6 months and concentration of the drug was calculated over the period of storage periodically by HPLC to find out which temperature is the most suitable for storage of both solution and nanoemulsion of DHA-SBT-1214 drug. As shown in FIG. 19A, nanoemulsion of DHA-SBT-1214 is stable at both 4° C. and −20° C. conditions but not at room temperature. However, drug solution of DHA-SBT-1214 was stable only at −20° C. storage condition but not at room temperature and 4° C. During this period of storage, physical characteristics of the nanoemulsion were also determined periodically. FIG. 19B showed 4° C. is an ideal storage condition at which particle size of the nanoemulsion stays almost constant but increased gradually at −20° C. and showed very large aggregates at room temperature. During this time, PDI (polydispersity index) was also determined, shown in FIG. 19C, and zeta potential (surface charge) was determined, shown in FIG. 19D, and it was concluded that 4° C. is the best storage condition for long term storage of nanoemulsion formulations.

Example 7

Further In Vivo Cytotoxicity Studies

These in vivo studies were focused on analyses of cytotoxicity of different doses of NE-DHA-SBT-1214. Animals were divided into the following groups (TABLE 3). Different doses of NE-DHA-SBT-1214 (30, 40, 50 and 70 mg/kg) were administered intravenously one time per week, for 3 weeks with 4 weeks follow-up observation.

TABLE 3

Experimental Groups

| Group Number | Condition | Number of Mice/Group |
|---|---|---|
| 1 | Control (no treatment) | 3 |
| 2 | NE-DHA-SBT 30 mg/kg | 4 |
| 3 | NE-DHA-SBT 40 mg/kg | 4 |
| 4 | NE-DHA-SBT 50 mg/kg | 3 |
| 5 | NE-DHA-SBT 70 mg/kg | 3 |

Dramatic suppression of tumor growth was observed (FIGS. 20A-20E) induced by all tested concentrations of the NE-DHA-SBT, which has motivated further evaluation of much lower doses of it. As previously, systemic toxicity was closely monitored and evaluated by standard criteria (motor activity, morbidity, appetite, posture and appearance) and tumor growth was measured weekly. One part of each mouse tumor xenograft was pre-treated with RNA-Later and kept at −80° C. before PCR arrays analysis of CSC-relevant genes expression (which will be done upon completion of the in vivo studies). Portion of each harvested tumor was mechanically and enzymatically disaggregated into single cell suspension as previously described and tested for ability to induce the round colonies (holoclones) and 3D spheroids (as a test for survival of CSCs).

Constant efforts were applied for maintenance, purification and propagation of highly clonogenic and tumorigenic population of the PPT2 cells, which are constantly used for in vivo and in vitro studies. Another set of NOD/SCID mice were transplanted with PPT2 cells for study of cytotoxicity of low doses of NE-DHA-SBT-1214.

Example 8

Figure 21:
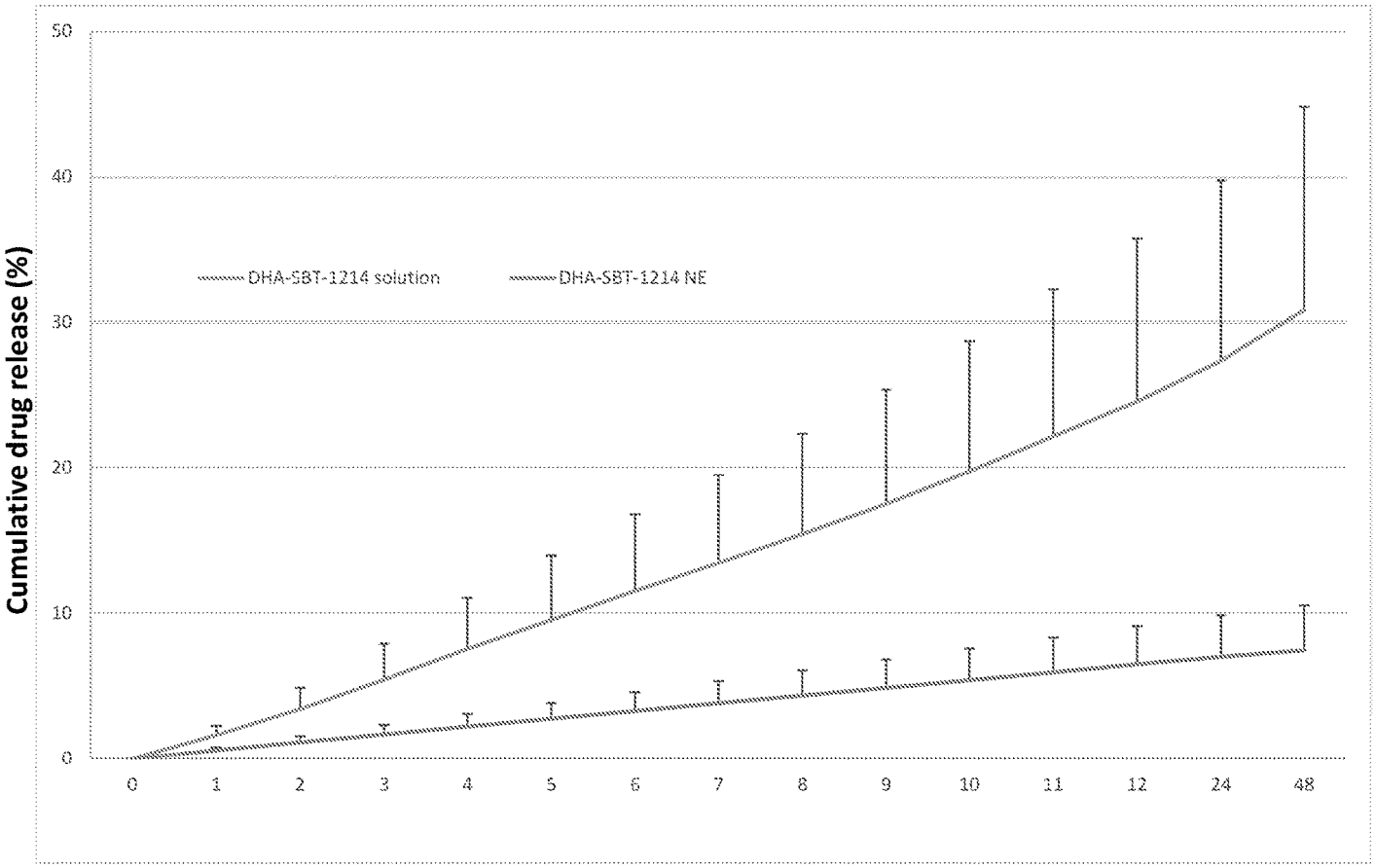
FIG. 21 is a graph of an in vitro dialysis release study of DHA-SBT-1214 from solution and nanoemulsions (NE), cumulative DHA-SBT-1214 release (%) from solution and NE is plotted against time (hours).

In Vitro Release of DHA-SBT-1214 from Drug Solution and Nanoemulsion Formulation In order to study the in vitro release profile of the drug solution and from its nanoemulsion formulation, 5 μg of DHA-SBT-1214 nanoemulsion or drug solution was injected in 3500 MWCO Slide-Lyzer Dialysis Cassette after being conditioned with dialysis buffer and suspended in PBS+ sodium lauryl sulfate (SLS) buffer for different points at 100 rpm rotation for 12 hours. 1 ml sample was taken out from the beaker after every hour and the drug was extracted with acetonitrile and ran HPLC to quantify the amount of drug release from both solution and nanoemulsion. As shown in FIG. 21, release of DHA-SBT-1214 is more than 3 times faster from drug solution compared to its nanoemulsion formulation.

The invention has been described in an illustrative manner, and it is to be understood that the terminology, which has been used is intended to be in the nature of words of description rather than of limitation. Obviously, many modifications and variations of the present invention are possible in light of the above teachings. It is, therefore, to be understood that within the scope of the appended claims, the invention can be practiced otherwise than as specifically described.

REFERENCES

Botchkina G I, Zuniga E S, Das M, Wang Y, Wang H, Zhu S, Savitt A G, Rowehl R A, Leyfman Y, Ju J, Shroyer K, Ojima I. New-generation taxoid SB-T-1214 inhibits stem cell-related gene expression in 3D cancer spheroids induced by purified colon tumor-initiating cells. Mol Cancer. (2010) Jul. 14; 9:192. doi:10.1186/1476-4598-9-192.

Botchkina G I, Zuniga E S, Rowehl R H, Park R, Bhalla R, Bialkowska A B, Johnson F, Golub L M, Zhang Y, Ojima I, Shroyer K R. Prostate cancer stem cell-targeted efficacy of a new-generation taxoid, SBT-1214 and novel polyenolic zinc-binding curcuminoid, CMC2.24. PLoS One. (2013) Sep. 24; 8(9):e69884. doi:10.1371/journal.pone.0069884.

Bradley M O, Webb N L, Anthony F H, Devanesan P, Witman P A, Hemamalini S, Chander M C, Baker S D, He L, Horwitz S B, Swindell C S. Tumor targeting by covalent conjugation of a natural fatty acid to paclitaxel. Clin Cancer Res. (2001) October; 7(10):3229-38.

Ferlini C, Distefano M, Pignatelli F, Lin S, Riva A, Bombardelli E, Mancuso S, Ojima I, Scambia G. Antitumour activity of novel taxanes that act at the same time as cytotoxic agents and P-glycoprotein inhibitors. Br J Cancer. (2000) December; 83(12):1762-8.

Ganta S, Devalapally H, Amiji M. Curcumin enhances oral bioavailability and anti-tumor therapeutic efficacy of paclitaxel upon administration in nanoemulsion formulation. J Pharm Sci. (2010) November; 99 (11): 4630-41. doi:10.1002/jps.22157.

Ganta S, Singh A, Patel N R, Cacaccio J, Rawal Y H, Davis B J, Amiji M M, Coleman T P. Development of EGFR-targeted nanoemulsion for imaging and novel platinum therapy of ovarian cancer. Pharm Res. (2014) September; 31 (9): 2490-502. doi:10.1007/s11095-014-1345-z. Epub 2014 Mar. 19.

Matesanz R, Trigili C, Rodriguez-Salarichs J, Zanardi I, Pera B, Nogales A, Fang W S, Jímenez-Barbero J, Canales A, Barasoain I, Ojima I, Díaz J F. Taxanes with high potency inducing tubulin assembly overcome tumoural cell resistances. Bioorg Med Chem. (2014) Sep. 15; 22(18):5078-90. doi: 10.1016/j.bmc.2014.05.048. Epub 2014 Jun. 19.

Ojima I, Zuniga E S, Berger W T, Seitz J D. Tumor-targeting drug delivery of new-generation taxoids. Future Med Chem. (2012) January; 4(1):33-50. doi: 10.4155/fmc.11.167.

"Drug Conjugates with Polyunsaturated Fatty Acids", J. Seitz and I. Ojima, In Drug Delivery in Oncology—From Research Concepts to Cancer Therapy (F. Kratz, P. Senter and H. Steinhagen Ed.) Wiley-VCH: Weinheim. Vol. 3. (2011) Chapter 5.9: pp 1323-1360.

Tiwari S B, Amiji M M. Improved oral delivery of paclitaxel following administration in nanoemulsion formulations. J Nanosci Nanotechnol. (2006) September-October; 6 (9-10): 3215-21.

Gupta P B, Chaffer C L, Weinberg R A. Cancer stem cells: mirage or reality? Nature medicine. 2009; 15(9):1010-2. doi: 10.1038/nm0909-1010. PubMed PMID: 19734877.

Gupta P B, Fillmore C M, Jiang G, Shapira S D, Tao K, Kuperwasser C, Lander E S. Stochastic state transitions give rise to phenotypic equilibrium in populations of cancer cells. Cell. 2011; 146(4):633-44. doi: 10.1016/j.ce11.2011.07.026. PubMed PMID: 21854987.

Hanahan D, Weinberg R A. Hallmarks of cancer: the next generation. Cell. 2011; 144(5):646-74. doi: 10.1016/j.ce11.2011.02.013. PubMed PMID: 21376230.

Fanali C, Lucchetti D, Farina M, Corbi M, Cufino V, Cittadini A, Sgambato A. Cancer stem cells in colorectal cancer from pathogenesis to therapy: controversies and perspectives. World journal of gastroenterology: WJG. 2014; 20(4):923-42. doi: 10.3748/wjg.v20.i4.923. PubMed PMID: 24574766; PMCID: 3921545.

Hermann P C, Huber S L, Herrler T, Aicher A, Ellwart J W, Guba M, Bruns C J, Heeschen C. Distinct populations of cancer stem cells determine tumor growth and metastatic activity in human pancreatic cancer. Cell stem cell. 2007; 1(3):313-23. doi: 10.1016/j.stem.2007.06.002. PubMed PMID: 18371365.

Goldstein A S, Huang J, Guo C, Garraway I P, Witte O N. Identification of a cell of origin for human prostate cancer. Science. 2010; 329(5991):568-71. doi: 10.1126/science.1189992. PubMed PMID: 20671189; PMCID: 2917982.

Miki J, Furusato B, Li H, Gu Y, Takahashi H, Egawa S, Sesterhenn I A, McLeod D G, Srivastava S, Rhim J S. Identification of putative stem cell markers, CD133 and CXCR4, in hTERT-immortalized primary nonmalignant and malignant tumor-derived human prostate epithelial cell lines and in prostate cancer specimens. Cancer research. 2007; 67(7):3153-61. doi: 10.1158/0008-5472.CAN-06-4429. PubMed PMID: 17409422.

Di C, Zhao Y. Multiple drug resistance due to resistance to stem cells and stem cell treatment progress in cancer (Review). Experimental and Therapeutic Medicine. 2015; 9(2):289-93. doi: 10.3892/etm.2014.2141. PubMed PMID: PMC4280950.

Lathia J D. Awakening the Beast: Chemotherapeutic Activation of Cancer Stem Cells. Science translational medicine. 2015; 7(269):269ec3-ec3. doi: 10.1126/scitranslmed.aaa3470.

Gelderblom H, Verweij J, Nooter K, Sparreboom A. Cremophor E L: the drawbacks and advantages of vehicle selection for drug formulation. European journal of cancer. 2001; 37(13):1590-8. PubMed PMID: 11527683.

Gianni L, Kearns C M, Giani A, Capri G, Vigano L, Lacatelli A, Bonadonna G, Egorin M J. Nonlinear pharmacokinetics and metabolism of paclitaxel and its pharmacokinetic/pharmacodynamic relationships in humans. Journal of clinical oncology: official journal of the American Society of Clinical Oncology. 1995; 13(1):180-90. PubMed PMID: 7799018.

Nooter K, Stoter G. Molecular Mechanisms of Multidrug Resistance in Cancer Chemotherapy. Pathology—Research and Practice. 1996; 192(7):768-80.

Vredenburg M R, Ojima I, Veith J, Pera P, Kee K, Cabral F, Sharma A, Kanter P, Bernacki R J. Effects of orally active taxanes on P-glycoprotein modulation and colon and breast carcinoma drug resistance. J Nat'l Cancer Inst. 2001; 93:1234-45.

Ojima I, Slater J C, Michaud E, Kuduk S D, Bounaud P-Y, Vrignaud P, Bissery M-C, Veith J, Pera P, Bernacki R J. Syntheses and Structure-Activity Relationships of the Second Generation Antitumor Taxoids. Exceptional Activity against Drug Resistant Cancer Cells. J Med Chem. 1996; 39:3889-96.

Ojima I, Slater J S, Kuduk S D, Takeuchi C S, Gimi R H, Sun C-M, Park Y H, Pera P, Veith J M, Bernacki R J. Syntheses and Structure-Activity Relationships of Taxoids Derived from 14β-Hydroxy-10-deacetylbaccatin III. J Med Chem. 1997; 40:267-78.

Ojima I, Wang T, Miller M L, Lin S, Borella C, Geng X, Pera P, Bernacki R J. Syntheses and Structure-Activity Relationships of New Second-Generation Taxoids. Bioorg Med Chem Lett. 1999; 9:3423-8.

Botchkina G I, Zuniga E S, Das M, Wang Y, Wang H, Zhu S, Savitt A G, Rowehl R A, Leyfman Y, Ju J, Shroyer K, Ojima I. New-generation taxoid SB-T-1214 inhibits stem cell-related gene expression in 3D cancer spheroids induced by purified colon tumor-initiating cells. Molecular cancer. 2010; 9:192. doi: 10.1186/1476-4598-9-192. PubMed PMID: 20630067; PMCID: 2911448.

Botchkina G I, Zuniga E S, Rowehl R H, Park R, Bhalla R, Bialkowska A B, Johnson F, Golub L M, Zhang Y, Ojima I, Shroyer K R. Prostate cancer stem cell-targeted efficacy of a new-generation taxoid, SBT-1214 and novel polyenolic zinc-binding curcuminoid, CMC2.24. PloS one. 2013; 8(9):e69884. doi: 10.1371/journal.pone.0069884. PubMed PMID: 24086245; PMCID: 3782470.

Botchkina I L, Rowehl R A, Rivadeneira D E, Karpeh M S, Jr., Crawford H, Dufour A, Ju J, Wang Y, Leyfman Y, Botchkina G I. Phenotypic subpopulations of metastatic colon cancer stem cells: genomic analysis. Cancer genomics & proteomics. 2009; 6(1):19-29. PubMed PMID: 19451087.

Ferlini C, Distefano M, Pignatelli F, Lin S, Riva A, Bombardelli E, Mancuso S, Ojima I, Scambia G. Antitumor Activity of Novel Taxanes That Act as Cytotoxic Agents and P-Glycoprotein Inhibitors at the Same Time. Brit J Cancer. 2000; 83:1762-8.

Ganta S, Amiji M. Coadministration of Paclitaxel and curcumin in nanoemulsion formulations to overcome multidrug resistance in tumor cells. Molecular pharmaceutics. 2009; 6(3):928-39. doi: 10.1021/mp800240j. PubMed PMID: 19278222.

Ganta S, Devalapally H, Amiji M. Curcumin enhances oral bioavailability and anti-tumor therapeutic efficacy of paclitaxel upon administration in nanoemulsion formulation. Journal of pharmaceutical sciences. 2010; 99(11): 4630-41. doi: 10.1002/jps.22157. PubMed PMID: 20845461.

van Vlerken L E, Duan Z, Little S R, Seiden M V, Amiji M M. Biodistribution and pharmacokinetic analysis of Paclitaxel and ceramide administered in multifunctional polymer-blend nanoparticles in drug resistant breast cancer model. Molecular pharmaceutics. 2008; 5(4):516-26. doi: 10.1021/mp800030k. PubMed PMID: 18616278; PMCID: 2646668.

Tiwari S B, Amiji M M. Improved oral delivery of paclitaxel following administration in nanoemulsion formulations. Journal of nanoscience and nanotechnology. 2006; 6(9-10):3215-21. PubMed PMID: 17048539.

Ganta S, Singh A, Patel N R, Cacaccio J, Rawal Y H, Davis B J, Amiji M M, Coleman T P. Development of EGFR-targeted nanoemulsion for imaging and novel platinum therapy of ovarian cancer. Pharmaceutical research. 2014; 31(9):2490-502. doi: 10.1007/s11095-014-1345-z. PubMed PMID: 24643932; PMCID: PMC4169355.

Chen J, Li Y, Yu T S, McKay R M, Burns D K, Kernie S G, Parada L F. A restricted cell population propagates glioblastoma growth after chemotherapy. Nature. 2012; 488 (7412):522-6. doi: 10.1038/nature11287. PubMed PMID: 22854781; PMCID: 3427400.

What is claimed is:

1. A composition comprising an omega-3 polyunsaturated fatty acid (PUFA)-taxoid conjugate *of DHA-SBT-1214* encapsulated in an oil-in-water nanoemulsion (NE) drug delivery system, wherein the oil comprises one or more omega fatty acids *and wherein said composition is formulated for parenteral administration*.

[2. The composition of claim 1, wherein said PUFA is chosen from the group consisting of docosahexaenoic acid (DHA), eicosapentaenoic acid (EPA), and alpha-linolenic acid (LNA).]

[3. The composition of claim 1, wherein said PUFA-taxoid conjugate is DHA-SBT-1214.]

[4. The composition of claim 1, wherein a taxoid in said PUFA-taxoid conjugate is chosen from the group consisting of paclitaxel, docetaxel, SBT-1213, SBT-12854, SBT-121303, SBT-1216, SBT-11033, SBT-121313, SBT-121602, cabazitaxel, SBT-1212, SBT-1217, SBT-1102, SBT-1103, SBT-1104, SBT-1106, SBT-1107, SBT-121301, SBT-121302, SBT-121304, SBT-121403, SBT-11031, SBT-11032, SBT-11034, SBT-12851, SBT-12852, SBT-12853, SBT-12855, SBT-12851-1, SBT-12851-3, SBT-12852-1, SBT-12852-3, SBT-12853-1, SBT-12853-3, SBT-12854-1, SBT-12854-3, SBT-12855-1, and SBT-12855-3.]

[5. The composition of claim 1, wherein said PUFA-taxoid conjugate is chosen from the group consisting of DHA-paclitaxel, DHA-docetaxel, DHA-SBT-1213, DHA-SBT-1103, DHA-SBT-1104, DHA-SBT-1216, LNA-SBT-1213, LNA-paclitaxel, LNA-docetaxel, DHA-cabazitaxel, and LNA-cabazitaxel.]

[6. The composition of claim 4, wherein said PUFA-taxoid conjugate is a DHA or LNA ester of said taxoid defined in claim 4.]

7. The composition of claim 1, wherein said oil-in-water NE includes mean droplet diameters ranging from 50 to 1000 nm.

8. The composition of claim 1, wherein said oil-in-water NE includes mean droplet diameters less than 200 nm.

9. The composition of claim 1, wherein an oil in said oil-in-water NE is an omega-3 fatty acid-rich edible oil chosen from the group consisting of fish oil, pine nut oil, flax-seed oil, [safflower oil,] primrose oil, black currant oil, borage oil, wheat germ oil, chia oil, hemp oil, perilla oil, grape oil, squalene oil, and fungal oil.

10. The composition of claim 1, wherein said oil is modified with a substance chosen from the group consisting of surfactants, targeting agents, image contrast agents, and combinations thereof.

[11. The composition of claim 1, wherein said PUFA-taxoid conjugate is encapsulated in nanoparticles.]

12. The composition of claim 1, wherein said composition is a pharmaceutical composition including pharmaceutically acceptable carriers.

13. The composition of claim 1, wherein said composition is physically stable at 4° C. for up to 6 months.

14. The composition of claim 13, wherein the composition has a stable particle size for up to 6 months.

15. The composition of claim 1, wherein said composition has increased retention times in the body than a solution form of said PUFA-taxoid conjugate.

16. The composition of claim 1, wherein said composition has a release profile that is at least three times slower in the body than a solution form of said PUFA-taxoid conjugate.

17. A method of treating cancer, including the steps of: administering *parenterally* an effective amount of a pharmaceutical composition including an omega-3 polyunsaturated fatty acid (PUFA)-taxoid conjugate *of DHA-SBT-1214* encapsulated in an oil-in-water NE drug delivery system, wherein the oil comprises one or more omega fatty acids *and wherein the composition is formulated for parenteral admin-*

*istration*, to a subject in need of treatment; and treating cancer chosen from the group consisting of colon, pancreatic, non-small cell lung, and prostate.

[18. The method of claim 17, wherein the PUFA is chosen from the group consisting of docosahexaenoic acid (DHA), eicosapentaenoic acid (EPA), and alpha-linolenic acid (LNA).]

[19. The method of claim 18, wherein the PUFA-taxoid conjugate is DHA-SBT-1214.]

[20. The method of claim 18, wherein a taxoid in the PUFA-taxoid conjugate is chosen from the group consisting of paclitaxel, docetaxel, SBT-1213, SBT-12854, SBT-121303, SBT-1216, SBT-11033, SBT-121313, SBT-121602, cabazitaxel, SBT-1212, SBT-1217, SBT-1102, SBT-1103, SBT-1104, SBT-1106, SBT-1107, SBT-121301, SBT-121302, SBT-121304, SBT-121403, SBT-11031, SBT-11032, SBT-11034, SBT-12851, SBT-12852, SBT-12853, SBT-12855, SBT-12851-1, SBT-12851-3, SBT-12852-1, SBT-12852-3, SBT-12853-1, SBT-12853-3, SBT-12854-1, SBT-12854-3, SBT-12855-1, and SBT-12855-3.]

[21. The method of claim 18, wherein the PUFA-taxoid conjugate is chosen from the group consisting of DHA-paclitaxel, DHA-docetaxel, DHA-SBT-1213, DHA-SBT-1103, DHA-SBT-1104, DHA-SBT-1216, LNA-SBT-1213, LNA-paclitaxel, LNA-docetaxel, DHA-cabazitaxel, and LNA-cabazitaxel.]

[22. The method of claim 20, wherein said PUFA-taxoid conjugate is a DHA or LNA ester of the taxoid defined in claim 20.]

23. The method of claim [19] *17*, further including the step of reducing the expression of stemness-promoting genes and transcription factors in cancer stem cells.

24. The method of claim 23, wherein the stemness-promoting genes are chosen from the group consisting of ABCG2, ACAN, ACTB, AIN1, ALDH1A1, ALPI, ASCL2, BMP1, BMP3, CCND1, CD3D, CD4, CD8A, CD8B, CD8B1, CDH2, COL1A1, COL2A1, COL9A1, CTNNA1, DHH, DLL1, DLL3, DTX1, DVL1, FGF1, FGF3, FGFR1, FZD1, GDF2, GDF3, GJA1, GJB1, IGF1, ISL1, JAG1, KRT15, MME, MSX1, MYOD, NEUROG2, NCAM1, NOTCH1, NUMB, PARD6A, PPARD, RB1, RPL13A, S100B, SOX1, SOX2, TERT and combinations thereof.

25. The method of claim 23, wherein the transcription factors are chosen from the group consisting of Sox-2, Oct3/4, c-Myc, Klf4, and combinations thereof.

26. The method of claim [19] *17*, further including the steps of reducing or eliminating a cancer stem cell component of a tumor, and rendering the tumor more susceptible to therapy.

27. The method of claim [19] *17*, further including the steps of rapidly polymerizing tubulin and inducing cell death.

28. The method of claim [19] *17*, further including the step of administering a [non-conjugated version of the PUFA-taxoid] *taxoid in combination with said* (*PUFA*)-*taxoid conjugate* to the subject.

29. The method of claim [19] *17*, wherein the subject has paclitaxel-sensitive or paclitaxel-resistant tumors.

30. The method of claim [19] *17*, further including the step of down-regulating expression of a gene selected from the group consisting of CDX2, DLX2, DNMT3B, EGR, FOXP3, GLI2, HOX family TFs, IRX4, JUN, KLF2, NFATC1, NR2F2, PCNA, PITX3, POU4F1, SIX2, SOX9, WT1, and combinations thereof.

31. The method of claim [19] *17*, further including the steps of suppressing tumor growth, inducing tumor shrinkage, reducing production of adherent holoclones, and reducing vascularization of the tumor.

32. The method of claim [19] *17*, wherein said administering step further includes the step of providing tumor-specific accumulation of composition through gp60-mediated transcytosis into tumor interstitium due to an affinity of the composition to human serum albumin.

33. The method of claim [19] *17*, further including the step of retaining the pharmaceutical composition in the subject for a longer period of time than a solution form of the pharmaceutical composition.

34. The method of claim 33, wherein the pharmaceutical composition is retained in a tumor in the subject for a longer period of time than a solution form of the pharmaceutical composition.

35. The method of claim [19] *17*, further including the step of providing a release profile of the pharmaceutical composition that is at least three times slower than a release profile of a solution form of the pharmaceutical composition.

36. A method of overcoming multi-drug resistance, including the steps of: exposing a multi-drug resistant cell selected from the group consisting of colon cancer cells and prostate cancer cells to an effective amount of a pharmaceutical composition including an omega-3 polyunsaturated fatty acid (PUFA)-taxoid conjugate *of DHA-SBT-1214* encapsulated in an oil-in-water NE drug delivery system, wherein the oil comprises one or more omega fatty acids *and wherein the composition is formulated for parenteral administration*; and inducing the death of the multi-drug resistant cell.

[37. The method of claim 36, wherein the PUFA-taxoid conjugate is DHA-SBT-1214.]

38. The method of claim 36, further including the step of reducing the expression of stemness-promoting genes and transcription factors in cancer stem cells.

39. The method of claim 38, wherein the stemness-promoting genes are chosen from the group consisting of ABCG2, ACAN, ACTB, AIN1, ALDH1A1, ALPI, ASCL2, BMP1, BMP3, CCND1, CD3D, CD4, CD8A, CD8B, CD8B1, CDH2, COL1A1, COL2A1, COL9A1, CTNNA1, DHH, DLL1, DLL3, DTX1, DVL1, FGF1, FGF3, FGFR1, FZD1, GDF2, GDF3, GJA1, GJB1, IGF1, ISL1, JAG1, KRT15, MME, MSX1, MYOD, NEUROG2, NCAM1, NOTCH1, NUMB, PARD6A, PPARD, RB1, RPL13A, S100B, SOX1, SOX2, TERT and combinations thereof.

40. The method of claim 38, wherein the transcription factors are chosen from the group consisting of Sox-2, Oct3/4, c-Myc, Klf4, and combinations thereof.

41. The method of claim 36, further including the steps of reducing or eliminating a cancer stem cell component of a tumor, and rendering the tumor more susceptible to therapy.

42. The method of claim 36, further including the steps of rapidly polymerizing tubulin and inducing cell death.

43. The method of claim 36, wherein the subject has paclitaxel-sensitive or paclitaxel-resistant tumors.

44. The method of claim 36, further including the step of down-regulating expression of a gene selected from the group consisting of CDX2, DLX2, DNMT3B, EGR, FOXP3, GLI2, HOX family TFs, IRX4, JUN, KLF2, NFATC1, NR2F2, PCNA, PITX3, POU4F1, SIX2, SOX9, WT1, and combinations thereof.

45. The method of claim 36, further including the steps of suppressing tumor growth, inducing tumor shrinkage, reducing production of adherent holoclones, and reducing vascularization of the tumor.

46. The method of claim 36, wherein said administering step further includes the step of providing tumor-specific accumulation of composition through gp60-mediated transcytosis into tumor interstitium due to an affinity of the composition to human serum albumin.

47. A method of eliminating a cancer stem cell, including the steps of: exposing a cancer stem cell selected from the group consisting of colon cancer stem cells and prostate cancer stem cells to an effective amount of a pharmaceutical composition including an omega-3 polyunsaturated fatty acid (PUFA)-taxoid conjugate *of DHA-SBT-1214* encapsulated in an oil-in-water NE drug delivery system, wherein the oil comprises one or more omega fatty acids *and wherein the composition is formulated for parenteral administration*; and inducing the death of the cancer stem cell.

[48. The method of claim 47, wherein the PUFA-taxoid conjugate is DHA-SBT-1214.]

49. A method of reducing the stemness of a cancer stem cell, including the steps of: exposing a cancer stem cell selected from the group consisting of colon cancer stem cells and prostate cancer stem cells to an effective amount of a pharmaceutical composition including an omega-3 polyunsaturated fatty acid (PUFA)-taxoid conjugate *of DHA-SBT-1214* encapsulated in an oil-in-water NE drug delivery system, wherein the oil comprises one or more omega fatty acids *and wherein the composition is formulated for parenteral administration*; and reducing the expression of stemness-promoting genes in the cancer stem cell.

[50. The method of claim 49, wherein the PUFA-taxoid conjugate is DHA-SBT-1214.]

51. A method of increasing retention times of an omega-3 polyunsaturated fatty acid (PUFA)-taxoid conjugate in the body of a subject, including the steps of: administering *parenterally* an effective amount of a pharmaceutical composition including an omega-3 polyunsaturated fatty acid (PUFA)-taxoid conjugate *of DHA-SBT-1214* encapsulated in an NE drug delivery system, wherein the oil comprises one or more omega fatty acids *and wherein the composition is formulated for parenteral administration*; and retaining the pharmaceutical composition in the body for a longer period of time than a solution form of the pharmaceutical composition.

52. The method of claim 51, wherein said retaining step is further defined as retaining the pharmaceutical composition in an area of the body chosen from the group consisting of plasma and a tumor for a longer period of time than a solution form of the pharmaceutical composition.

53. A method of providing a slower release profile of an omega-3 polyunsaturated fatty acid (PUFA)-taxoid conjugate in the body of a subject, including the steps of: administering *parenterally* an effective amount of a pharmaceutical composition including an omega-3 polyunsaturated fatty acid (PUFA)-taxoid conjugate *of DHA-SBT-1214* encapsulated in an NE drug delivery system, wherein the oil comprises one or more omega fatty acids *and wherein the composition is formulated for parenteral administration*; and releasing the pharmaceutical composition in the body at least three times slower than a solution form of the pharmaceutical composition.

*54. A composition having a taxoid-conjugate encapsulated in a nanoemulsion (NE) drug delivery system,*

*wherein the taxoid-conjugate comprises a SBT-1214;*

*wherein the taxoid-conjugate comprises an omega-3 polyunsaturated fatty acid (PUFA);*

*wherein the taxoid-conjugate is encapsulated in the NE drug delivery system and formulated for parenteral administration;*

*wherein the NE drug delivery system comprises an aqueous phase and an oil/lipid phase; and*

*wherein the taxoid-conjugate is released from the NE delivery system in a formulation more slowly than the taxoid-conjugate is released from the formulation lacking the NE delivery system.*

*55. The composition of claim 54, wherein said NE drug delivery system has an oil/lipid phase comprising droplets having a mean diameter ranging from 50 to 1000 nm.*

*56. The composition of claim 54, wherein said NE drug delivery system has an oil/lipid phase comprising droplets having a mean diameter of 200 nm.*

*57. The composition of claim 54, wherein said oil/lipid phase is an omega-3 fatty acid-rich edible oil chosen from the group consisting of fish oil, pine nut oil, flax-seed oil, primrose oil, black currant oil, borage oil, wheat germ oil, chia oil, hemp oil, perilla oil, grape oil, squalene oil, and fungal oil.*

*58. The composition of claim 54, wherein said NE drug delivery system is modified with a substance chosen from the group consisting of surfactants, targeting agents, and image contrast agents, or combinations thereof.*

*59. The composition of claim 58, wherein said surfactant is polysorbate 80.*

*60. The composition of claim 54, wherein said composition is a pharmaceutical composition including pharmaceutically acceptable carriers.*

*61. The composition of claim 54, wherein said composition is physically stable at 4° C. for up to 6 months, and has a stable particle size for up to 6 months.*

*62. The composition of claim 54, wherein said composition has increased retention times in the body than a solution form of said taxoid-conjugate.*

*63. The composition of claim 54, wherein said taxoid-conjugate is released from the NE delivery system in a formulation at least three times more slowly than the taxoid-conjugate is released from the formulation lacking the NE delivery system.*

*64. A method of treating a subject having cancer, said method comprising administering parenterally to the subject a therapeutically effective amount of the composition of claim 54.*

*65. The method of claim 64, wherein the cancer is breast, ovary, lung, head and neck, colon, rectal, pancreatic, melanoma, brain, prostate, leukemia, sarcomas, thyroid, Non-Hodgkin Lymphoma, bladder, gliomas, endometrial, or renal cancer.*

*66. The method of claim 64, wherein expression of stemness-promoting genes and transcription factors in a stem cell in the cancer is reduced, wherein the stemness-promoting genes are chosen from the group consisting of ABCG2, ACAN, ACTB, AIN1, ALDH1A1, ALPI, ASCL2, BMP1, BMP3, CCND1, CD3D, CD4, CD8A, CD8B, CD8B1, CDH2, COL1A1, COL2A1, COL9A1, CTNNA1, DHH, DLL1, DLL3, DTX1, DVL1, FGF1, FGF3, FGFR1, FZD1, GDF2, GDF3, GJA1, GJB1, IGF1, ISL1, JAG1, KRT15, MME, MSX1, MYOD, NEUROG2, NCAM1, NOTCH1, NUMB, PARD6A, PPARD, RB1, RPL13A, S100B, SOX1, SOX2, and TERT, or combinations thereof, and wherein the transcription factors are chosen from the group consisting of Sox-2, Oct3/4, and c-Myc, Klf4, or combinations thereof.*

*67. The method of claim 64, wherein cancer stem cells of the cancer are reduced or eliminated rendering the tumor more susceptible to therapy, and wherein the tubulin of the cancer rapidly polymerizes, inducing cell death.*

*68. The method of claim 64, wherein the subject has a paclitaxel-sensitive tumor.*

*69. The method of claim 64, wherein a gene chosen from the group consisting of CDX2, DLX2, DNMT3B, EGR, FOXP3, GLI2, HOX family TFs, IRX4, JUN, KLF2, NFATC1, NR2F2, PCNA, PITX3, POU4F1, SIX2, SOX9, and WT1, and combinations thereof of a cancer cell of the cancer are down-regulated.*

*70. The method of claim 64, wherein the method results in suppression of tumor growth, induction of tumor shrinkage, reduction production of adherent holoclones, or reduction vascularization of the tumor and wherein the taxoid-conjugate is DHA-SBT-1214.*

*71. The method of claim 64, wherein the taxoid-conjugate is released from the NE delivery system in a formulation more slowly than the taxoid-conjugate is released from the formulation lacking the NE delivery system.*

*72. The method of claim 64, wherein the taxoid-conjugate is retained in the tumor for a longer period of time than a solution form of the pharmaceutical composition and wherein the taxoid-conjugate is released from the NE delivery system in a formulation at least three times more slowly than the taxoid-conjugate is released from a formulation lacking the NE delivery system.*

*73. A method of claim 64, wherein the cancer is a multi-drug resistant cancer.*

*74. The method of claim 73, wherein expression of stemness-promoting genes and transcription factors in a stem cell in the cancer is reduced, wherein the stemness-promoting genes are chosen from the group consisting of ABCG2, ACAN, ACTB, AIN1, ALDH1A1, ALPI, ASCL2, BMP1, BMP3, CCND1, CD3D, CD4, CD8A, CD8B, CD8B1, CDH2, COL1A1, COL2A1, COL9A1, CTNNA1, DHH, DLL1, DLL3, DTX1, DVL1, FGF1, FGF3, FGFR1, FZD1, GDF2, GDF3, GJA1, GJB1, IGF1, ISL1, JAG1, KRT15, MME, MSX1, MYOD, NEUROG2, NCAM1, NOTCH1, NUMB, PARD6A, PPARD, RB1, RPL13A, S100B, SOX1, SOX2, and TERT, and combinations thereof, and wherein the transcription factors are chosen from the group consisting of Sox-2, Oct3/4, c-Myc, and Klf4, or combinations thereof, and wherein the cancer stem cells of the cancer are reduced or eliminated rendering the tumor more susceptible to therapy and wherein the tubulin of the cancer rapidly polymerizes, inducing cell death.*

*75. The method of claim 64, wherein the subject has a paclitaxel-resistant tumor or paclitaxel-sensitive tumor.*

*76. The method of claim 73, wherein a gene chosen from the group consisting of CDX2, DLX2, DNMT3B, EGR, FOXP3, GLI2, HOX family TFs, IRX4, JUN, KLF2, NFATC1, NR2F2, PCNA, PITX3, POU4F1, SIX2, SOX9, and WT1, and combinations thereof of a cancer cell of the cancer is down-regulated, and wherein the method results in suppression of tumor growth, induction tumor shrinkage, reduction production of adherent holoclones, or reduction vascularization of the tumor.*

*77. The method of claim 73, wherein the cancer is breast, pancreatic, prostate, colon, or rectal, and wherein the composition is the composition of claim 54.*

*78. A method of reducing the stemness of a cancer stem cell, comprising the steps of:*

*exposing a cancer stem cell selected from the group consisting of colon cancer stem cells and prostate cancer stem cells to an effective amount of the composition of claim 54.*

*79. The composition of claim 54, wherein the aqueous phase comprises egg phosphatidylcholine (E-80), polysorbate 80, DSPE-PEG2000 and water.*

*80. The composition of claim 54, wherein the aqueous phase comprises egg phosphatidylcholine (E-80), polysorbate 80, DSPE-PEG2000 and water.*

*81. The composition of claim 80, wherein the oil/lipid phase comprises an omega-3 fatty acid-rich oil selected from the group consisting of fish oil, pine nut oil, flax-seed oil, primrose oil, black currant oil, borage oil, wheat germ oil, chia oil, hemp oil, perilla oil, grape oil, squalene oil, and fungal oil.*

*82. The composition of claim 54, wherein the NE delivery system further comprises a modifier selected from the group consisting of surfactants, targeting agents, and image contrast agents.*

*83. The composition of claim 81, wherein the NE delivery system further comprises a modifier selected from the group consisting of surfactants, targeting agents, and image contrast agents.*

*84. The composition of claim 54, wherein the taxoid-conjugate is released from the NE delivery system in an amount chosen from the group consisting of less than 10% in the course of 5 hours, less than 10% in the course of 10 hours, and less than 10% in the course of 48 hours.*

*85. The composition of claim 80, wherein the DHA-SBT-1214 is released from the NE delivery system in an amount chosen from the group consisting of less than 10% in the course of 5 hours, less than 10% in the course of 10 hours, and less than 10% in the course of 48 hours.*

*86. The composition of claim 54, wherein the NE delivery system maintains at least 80% of its original concentration of the taxoid-conjugate upon storage under conditions of 4° C. for an amount chosen from the group consisting of at least 2 months, at least 3 months, and at least 6 months.*

*87. The composition of claim 80, wherein the NE delivery system maintains at least 80% of its original concentration of DHA-SBT-1214 upon storage under conditions of 4° C. for an amount chosen from the group consisting of at least 2 months, at least 3 months, and at least 6 months.*

*88. A pharmaceutical composition comprising the composition of claim 54.*

*89. A pharmaceutical composition comprising the composition of claim 80.*

*90. The method of claim 64, wherein the cancer is resistant to 5-FU, oxaliplatin, irinotecan, docetaxel, or cabazitaxel.*

* * * * *